United States Patent
Aki et al.

(10) Patent No.: US 10,087,201 B2
(45) Date of Patent: *Oct. 2, 2018

(54) HYDROLYSIS CATALYST AND PROCESS

(71) Applicant: INVISTA NORTH AMERICA S.A R.L., Wilmington, DE (US)

(72) Inventors: Sudhir Aki, Katy, TX (US); Thomas E. Vos, Beaumont, TX (US)

(73) Assignee: INVISTA NORTH AMERICA S.A R.L., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/404,030

(22) PCT Filed: May 24, 2013

(86) PCT No.: PCT/US2013/042613
§ 371 (c)(1),
(2) Date: Nov. 26, 2014

(87) PCT Pub. No.: WO2013/181092
PCT Pub. Date: Dec. 5, 2013

(65) Prior Publication Data
US 2015/0158892 A1    Jun. 11, 2015

Related U.S. Application Data

(60) Provisional application No. 61/654,554, filed on Jun. 1, 2012.

(51) Int. Cl.
*C07F 9/145* (2006.01)
*C07F 9/6574* (2006.01)
*B01J 31/18* (2006.01)

(52) U.S. Cl.
CPC .......... *C07F 9/145* (2013.01); *B01J 31/185* (2013.01); *C07F 9/65744* (2013.01); *B01J 2231/322* (2013.01)

(58) Field of Classification Search
None
See application file for complete search history.

(56) References Cited

U.S. PATENT DOCUMENTS

| | | | |
|---|---|---|---|
| 3,655,723 A | 4/1972 | Drinkard, Jr. | |
| 5,886,235 A | 3/1999 | Bryant et al. | |
| 5,981,722 A | 11/1999 | Chen et al. | |
| 6,169,198 B1 | 1/2001 | Fischer et al. | |
| 7,470,805 B2 | 12/2008 | Rosier et al. | |
| 7,629,484 B2 | 12/2009 | Ritter | |
| 7,659,422 B2 | 2/2010 | Foo et al. | |
| 7,977,502 B2 | 7/2011 | Foo et al. | |
| 9,834,505 B2 | 12/2017 | Aki et al. | |
| 2004/0122251 A1* | 6/2004 | Rosier ............. | C07C 253/10 558/348 |
| 2007/0219386 A1* | 9/2007 | Ritter ............... | C07F 9/025 558/146 |
| 2009/0182164 A1 | 7/2009 | Foo et al. | |
| 2010/0267990 A1 | 10/2010 | Ritter et al. | |
| 2011/0196168 A1 | 8/2011 | Ostermaier | |

FOREIGN PATENT DOCUMENTS

| | | |
|---|---|---|
| WO | 2011/075494 A1 | 6/2011 |
| WO | 2011/075496 A1 | 6/2011 |
| WO | 2011/087688 A1 | 7/2011 |
| WO | 2012/005910 A1 | 1/2012 |
| WO | 2012/033556 A1 | 3/2012 |
| WO | 2013/181092 A1 | 12/2013 |

OTHER PUBLICATIONS

CAS email.*
Extended European Search Report Received for European Patent Application No. 13797289.9, dated May 3, 2016, 7 pages.
Supplementary European Search Report Received for European Patent Application No. 13797289.9, dated May 23, 2016, 1 page.
"European Application Serial No. 13797289.9, response dated Dec. 1, 2016.", 29 pgs.
International Preliminary Report on Patentability received for PCT Patent Application No. PCT/US2013/042613, dated Dec. 11, 2014, 6 pages.
International Search Report and Written Opinion received for PCT Patent Application No. PCT/US2013/042613, dated Aug. 12, 2013, 8 pages.

* cited by examiner

*Primary Examiner* — Yun Qian
(74) *Attorney, Agent, or Firm* — Robert B. Furr, Jr.

(57) ABSTRACT

A process of hydrolyzing a monodentate, bidentate or tridentate phosphorus-based phosphite ester ligand or ligand blend for a transition metal catalyst comprising contacting the ligand or ligand blend with a hydrolysis catalyst of the formula $(R_{11}X_{11})_nP(OH)_{3-n}$ where n is 0, 1 or 2 wherein the ligand or ligand blend comprises one or more of (i) a bidentate biphosphite ligand of formula (III), $(R^{12}-X^{12})(R^{13}-X^{13})P-X^{14}-Y-X^{24}-P(X^{22}-R^{22})(X^{23}-R^{23})$, (ii) a tridentate triphosphite ligand of formula (IIIA) $(R^{12}-X^{12})(R^{13}-X^{13})P-X^{14}-Y-X^{32}-P(X^{34}-R^{34})-(X^{33}-Y^2-K^{24}-P(X^{23}-R^{23})-(X^{22}-R^{22})$ or (iii) a monodentate phosphite ligand of formula (IV) $P(X^1-R^1)(X^2-R^2)(X^3-R^3)$ where each X is oxygen or a bond and each Y is an optionally substituted C6-C20 arylene, followed by separation of the ligand hydrolysis products.

15 Claims, No Drawings

HYDROLYSIS CATALYST AND PROCESS

CROSS-REFERENCE TO RELATED APPLICATION

This application claims the benefit of priority from U.S. Provisional Application No. 61/654,554, filed Jun. 1, 2012. This application hereby incorporates by reference this provisional application in its entirety.

FIELD OF THE INVENTION

The invention relates to the regulation of the composition of liquid phosphite blends, such as those utilized as catalyst components in the hydrocyanation reactions of 1,3-butadiene to produce 3-pentenenitriles and other unsaturated nitriles. More particularly, this invention relates to the adjustment of process parameters of treatment of ligands used as part of a hydrocyanation catalyst composed of a nickel and at least one bidentate phosphate ligand.

BACKGROUND OF THE INVENTION

U.S. Pat. No. 6,169,198 describes the process of hydrocyanation (reaction with HCN) of butadiene (BD) to prepare adiponitrile (ADN), and explains that the process can generally be divided into three steps. First, mononitriles such as 3-pentenenitrile (3-PN) are formed by the reaction of HCN with BD, along with other nitriles, including isomers which must be isomerized in subsequent steps to achieve the desired straight chain ADN as a final product. Second is the isomerization of species such as 2-methyl-3-butenenitrile (2M3BN). Third is a second hydrocyanation of the pentenenitriles to yield the desired ADN.

U.S. Pat. No. 5,981,722 describes and exemplifies a new class of catalysts for such transformations by the use of diphosphite nickel complexes for the hydrocyanation and isomerizations. This class of catalysts is characterized by greater catalytic activity and resistance to HCN-derived degradation reactions.

U.S. Pat. No. 7,470,805 describes a process of hydrocyanation of diolefins in the presence of a catalytic system comprising a transition metal and mono- and pluri-dentate organophosphorus ligands. According to this, the use of a mixture of two ligands, monodentate and pluri (bi and/or tri)dentate, enables the pluridentate ligand to be preserved in the reaction milieu.

Monodentate and bidentate phosphorus-based ligands, depicted as formulae (7) and (8), and (3), respectively, as the structures are termed in U.S. Pat. No. 7,629,484, can be used in preparation of a transition metal-organophosphorus catalyst for reactions such as hydrocyanation.

Monodentate Ligand Examples of U.S. Pat. No. 7,629,484

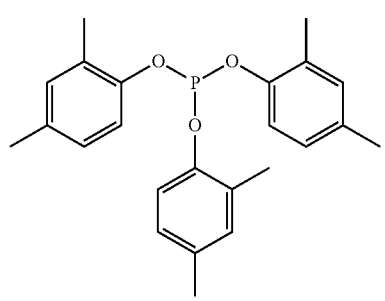

7

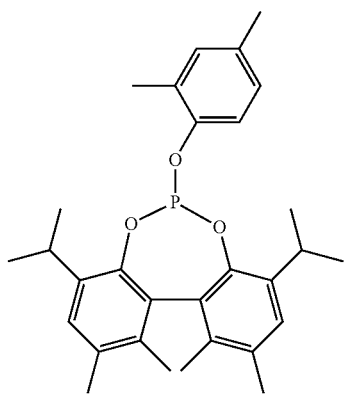

8

Bidentate Ligand Example of U.S. Pat. No. 7,629,484

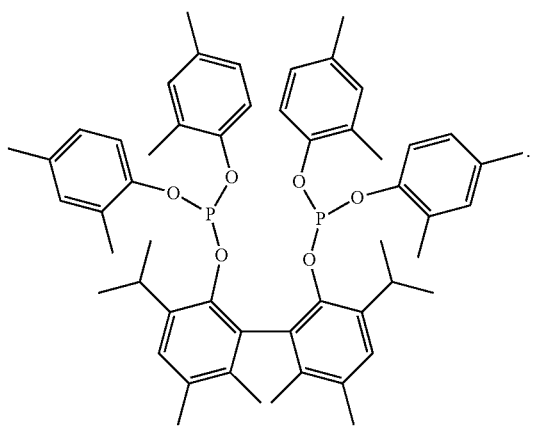

3

U.S. Pat. No. 7,659,422 describes a hydrocyanation process to produce ADN from BD with control of i) the overall feed molar ratio of 2-pentenenitriles to all unsaturated nitriles and ii) the overall feed molar ratio of HCN to all unsaturated nitriles. An example is given as a reaction mixture comprising a Lewis acid promoter ($FeCl_2$) and bidentate Ligand B, which as depicted is identical to Compound (3) above.

U.S. Pat. No. 7,977,502 describes an integrated, continuous process for the production of 3-PN, the refining of 3-PN and the refining of 2M3BN by a process comprising contacting a feed stream in a reaction zone, maintaining residence time to convert about 95% or more of the HCN, distilling to create various streams.

U.S. Published Patent Application No. 2011/0196168 describes nickel-containing solids comprising nickel metal derived from basic nickel carbonates (BNCs) which are highly reactive with both monodentate and bidentate phosphorus-containing ligands in forming nickel metal complexes, which can be for producing pentenenitriles and dinitriles by hydrocyanation.

SUMMARY OF THE INVENTION

The invention can include processes using selective hydrolysis of certain phosphorus-based ligands in a ligand blend or mixture to control relative proportions of monodentate versus bidentate and tridentate ligands. The ligand blend can be used to form transition metal complexes, such as nickel complexes, useful for catalysis of organic reactions, such as the hydrocyanation reaction providing nitriles from olefins such as 1,3-butadiene. The ligand hydrolysis reactions can be auto-catalyzed by ligand hydrolysis products formed in hydrocyanation reaction milieu where even trace or controlled amounts of water are present.

The invention can include a process of hydrolyzing a phosphorus-based ligand for a transition metal catalyst, wherein the ligand comprises at least one phosphite ester group; the process comprising:

i) contacting a hydrolysis catalyst of formula (I)

$$(R^{11}X^{11})_nP(OH)_{3-n} \qquad (I)$$

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{11}$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring;

with one or more phosphorus-based ligands selected from the group consisting of:

a bidentate phosphorus-based ligand of formula (III)

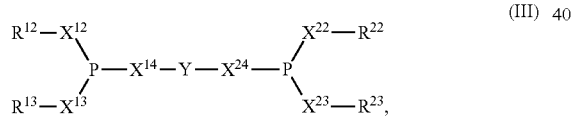

a tridentate phosphorus-based ligand of formula (IIIA)

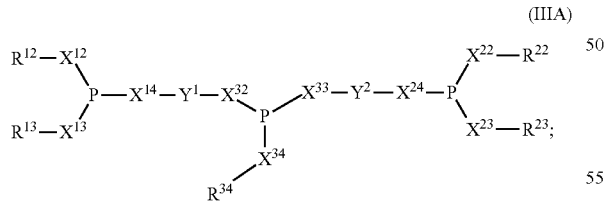

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

and a monodentate phosphorus-based ligand of formula (IV)

$$P(X^1R^1)(X^2R^2)(X^3R^3) \qquad (IV)$$

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^1$, $R^2$, or $R^3$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring; and a mixture thereof;

in the presence of water and, optionally, one or more organic liquids, under conditions of time, temperature, and concentration sufficient to bring about hydrolysis of the at least one phosphite ester bond to provide a hydrolysis product; and ii) separating the hydrolysis catalyst and the hydrolysis product from the ligand by liquid-liquid extraction.

The invention can provide a process for modifying the relative ratio of two phosphorus-based ligands for a transition metal catalyst, wherein each ligand in the blend comprises at least one phosphite ester group, in a ligand blend comprising at least two phosphorus-based ligands, a first component of the blend being selected from the group consisting of a bidendate phosphorus-based ligand of formula (III) and a tridentate phosphorus-based ligand of formula (IIIA):

a bidentate phosphorus-based ligand of formula (III)

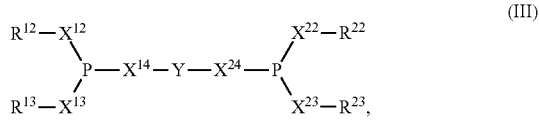
(III)

a tridentate phosphorus-based ligand of formula (IIIA)

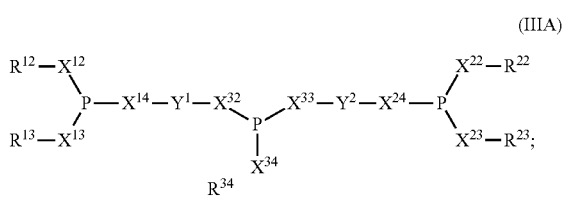
(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{14}$, $X^{14}$, $X^{24}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl; and a mixture thereof; and, a second component of the blend being a ligand comprising a monodentate phosphorus-based ligand of formula (IV)

$P(X^1R^1)(X^2R^2)(X^3R^3)$ (IV)

wherein $X^1$, $X^2$ and $X^3$ are each independently oxygen or a bond, provided that at least one of $X^a$, $X^2$, or $X^3$ is an oxygen; and $R^1$, $R^2$ and $R^3$ is each independently (C1-C10) alkyl, (C3-C10)cycloalkyl, (C3-C10)cycloalkyl(C1-C10) alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$, each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

the process comprising:

i) selectively hydrolyzing a phosphite ester group of the second component of the ligand blend with respect to a phosphite ester group of the first component of the ligand blend, by contacting the blend with a hydrolysis catalyst of formula (I)

$(R^{11}X^{11})_nP(OH)_{3-n}$ (I)

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{11}$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring; in the presence of water and, optionally, one or more organic liquids, under conditions of time, temperature, and concentration sufficient to bring about hydrolysis of the at least one phosphite ester bond of the second component to provide a hydrolysis product, and ii) separating the hydrolysis catalyst and the hydrolysis product from the ligand blend by liquid-liquid extraction.

The invention can provide a process for maintaining a concentration of a phosphorus-based bidentate ligand or of a phosphorus-based tridentate ligand, or both, within a concentration range, in a phosphorus-based ligand blend further comprising a monodentate phosphorus-based ligand, for a transition metal catalytic complex in a hydrocyanation reaction milieu comprising water and at least one organic liquid, wherein each phosphorus-based ligand in the blend comprises at least one phosphite ester group, the ligand blend comprising at least two phosphorus-based ligands, a first component of the ligand blend being a bidendate phosphorus-based ligand of formula (III) or a tridentate phosphorus-based ligand of formula (IIIA):

a bidentate phosphorus-based ligand of formula (III)

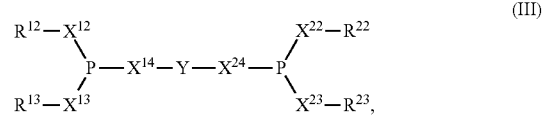
(III)

a tridentate phosphorus-based ligand of formula (IIIA)

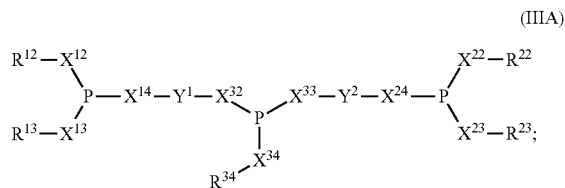

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl; and, a second component of the blend being a ligand comprising a monodentate phosphorus-based ligand of formula (IV)

$P(X^1R^1)(X^2R^2)(X^3R^3)$ (IV)

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^1$, $R^2$, or $R^3$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring; the process comprising:

i) contacting the ligand blend in the hydrocyanation reaction milieu with a hydrolysis catalyst of formula (I)

$(R^{11}X^{11})_nP(OH)_{3-n}$ (I)

wherein n is 0, 1, or 2, and each $X^{11}$ is independently oxygen or a bond, and each independently selected $R^1$ is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{11}$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring;

such that selective hydrolysis of a phosphite ester group of the monodentate ligand of formula (IV) in the ligand blend with respect to hydrolysis of a phosphite ester group of the bidentate ligand of formula (III) or the tridentate ligand of formula (IIIA) in the ligand blend occurs, to provide a hydrolysis product; and, ii) separating the hydrolysis catalyst and the hydrolysis product from the ligand blend by liquid-liquid extraction, such that a concentration of the bidentate ligand is maintained within the concentration range.

For example, the phosphorus-based ligand comprising at least one phosphite ester group can be a component of a phosphorus-based ligand blend, wherein the ligands contain at least one phosphite ester group, that are used in the presence of a transition metal, such as nickel, for catalysis of an olefin hydrocyanation reaction. For example, the ligand blend can be used in conjunction with the nickel for the hydrocyanation of 1,3-butadiene to yield pentenenitriles such as 3-pentenenitrile, an important intermediate in the synthesis of adiponitrile, or in the further hydrocyanation of pentenenitrile to yield adiponitrile, useful in manufacture of various nylon polymers. The invention can provide processes whereby liquid blends (mixtures) of phosphorus-based ligands, each containing at least one hydrolyzable phosphite ester group, wherein the blend includes at least one monodentate ligand (e.g., of formula (IV)) and at least one bidentate ligand (e.g., of formula (III)) or tridentate ligand (e.g., of formula (IIIA)), can be adjusted in the relative content of the ligands by monitoring the concentration of hydrolysis catalyst (e.g., of formula (I)), and selectively hydrolyzing and separating, for example, a selectively hydrolyzed monodentate ligand in the presence of a bidentate and/or tridentate ligand. The hydrolysis catalyst can be a ligand hydrolysis product produced by in situ hydrolysis of one or more ligand components of the blend. Also, the hydrolysis catalyst can, if appropriate, be added to the ligand blend, thereby preferentially hydrolyzing particular phosphites, e.g., monodentate ligands with respect to bidentate or tridentate ligands. The ligand blend can be present in the hydrocyanation reaction milieu and, as part of a catalyst maintenance subprocess, be adjusted in relative ligand concentrations through this selective hydrolysis and separation of certain ligand blend components.

Accordingly, the present invention can provide technical solutions to the problem of regulating the proportions of phosphorus-based ligands in a ligand blend for use in a transition metal complex for hydrocyanation reactions, such as when the hydrocyanation reactions are carried out in the presence of even trace or controlled amounts of water. Solutions to regulation of levels of monodentate versus bidentate and/or tridentate phosphorus-based ligands in ligand blends are provided that enable the formation of catalysts, e.g., nickel complexes with the ligands of the blend, with favorable properties for use in hydrocyanation reactions. Hydrolysis catalysts are provided, which can be derived by hydrolysis of monodentate phosphorus-based ligands, that can selectively hydrolyze monodentate ligands containing at least one phosphite ester bond in the presence of bidentate and/or tridentate ligands containing at least one phosphite ester bond, such that the acidic hydrolysis products of the monodentate ligands can be extracted, such as by liquid-liquid extraction using polar and nonpolar solvents, from the ligand blend, thereby maintaining higher relative concentrations of favorable bidentate/tridentate ligands.

DETAILED DESCRIPTION OF THE INVENTION

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

Aspects of the present disclosure employ, unless otherwise indicated, techniques of chemistry, and the like, which are within the skill of the art. Such techniques are explained fully in the literature. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

An "organic radical" or "organic group", as the term is used herein, refers to a portion or fragment or moiety, capable of bonding to another atom, wherein the group is carbon-based. By "carbon-based" is meant that at least a portion of the group comprises at least one carbon atom, which can be covalently bonded to other atoms capable of covalent bonding such as hydrogen, nitrogen, oxygen, halogen, sulfur, phosphorus, and the like, as is well known in the art.

When a group, e.g., an "alkyl" group or an "aryl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded.

Standard abbreviations for chemical groups such as are well known in the art can be used herein, and are within ordinary knowledge; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

Substituent groups J can independently be halo, nitro, cyano, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S) NR$_2$, and SC(S)NR$_2$; and so forth.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

Alkyl groups include straight chain and branched alkyl groups and cycloalkyl groups having from 1 to about 20 carbon atoms, and typically from 1 to 12 carbons or, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. The cycloalkyl group can have 3 to about 8-12 ring members, or, the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

Aryl groups are cyclic aromatic hydrocarbons that do not contain heteroatoms in the ring.

Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. Aryl groups can contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above. Aryl groups can also bear fused rings, such as fused cycloalkyl rings, within the meaning herein. For example, a tetrahydronaphthyl ring is an example of an aryl group within the meaning herein. Accordingly, an aryl ring includes, for example, a partially hydrogenated system, which can be unsubstituted or substituted, and includes one or more aryl rings substituted with groups such as alkyl, alkoxyl, cycloalkyl, cycloalkoxyl, cycloalkylalkyl, cycloalkoxyalkyl, and the like, and also fused with, e.g., a cycloalkyl ring.

Organophosphorus compounds include molecular entities wherein one or more phosphorus atoms is present, and one or more organic radicals or moieties is also present. An organophosphorus compound can further include other elements such as oxygen, halogens, hydrogen, nitrogen, and the like. Some terms in common usage for various classes of organophosphorus compounds, wherein P is a phosphorus atom and R indicates an organic moiety that is bonded via a carbon-phosphorus bond to the phosphorus atom, include "phosphine" ($PR_3$), "phosphine oxide" ($P(O)R_3$), "phosphinite" ($P(OR)R_2$), "phosphonite" ($P(OR)_2R$), "phosphinate" ($ROP(O)R_2$), "phosphite" ($P(OR)_3$), "phosphonate" ($RP(O)(OR)_2$), and "phosphate" ($P(O)(OR)_3$).

A "phosphorus-based ligand" as the term is used herein refers to a ligand containing at least one phosphorus atom, that is suitable for formation of a complex with a transition metal such as nickel, wherein the complex can possess catalytic activity for an organic reaction such as a hydrocyanation reaction of an olefin, such as the hydrocyanation of butadiene to yield pentenenitrile, or the hydrocyanation of pentenenitrile to yield adiponitrile. The term "phosphorus-based" refers to an organic compound that contains at least one phosphorus atom, whether or not it has catalytic activity.

A "monodentate" phosphorus-based ligand contains a single phosphorus atom per molecule, which can complex a metal atom such as nickel. A "bidentate" phosphorus-based ligand contains two phosphorus atoms per molecule, both of which can complex a single metal atom, such as a nickel atom. A "tridentate" phosphorus-based ligand contains three phosphorus atoms per molecule, all three of which can complex a single metal atom, such as a nickel atom.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The compound or set of compounds, such as are used in the inventive methods, can be any one of any of the combinations and/or sub-combinations of the elements as described herein.

A compound as shown in any of the Examples, or among the exemplary compounds, is provided.

Provisos can apply to any of the disclosed categories wherein any one or more of the other above disclosed categories or species can be excluded from such categories.

Hydrocyanation of Butadiene

The hydrocyanation of butadiene (BD) to yield adiponitrile (ADN) directly or indirectly through isomerization and/or additional hydrocyanation of intermediates with modern phosphorus-containing catalysts set forth below is well known in the art as evidenced by U.S. Pat. Nos. 7,977,502; and 7,659,422 and U.S. Published Applications 2009/0182164 and 2010/0267990. Various modifications can be used alone or in combination to achieve the desired efficiency with the selected components of the reaction. Thus, separation steps, temperatures, refining, distillation, isomerization zones, pressures, elimination of constituents along the pathway, column sizes and configurations, stream velocities, recycling, and other process variables can be adjusted to modify the overall ADN production as required.

The catalyst composition can be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, can be used to dissolve to the catalyst composition.

The HCN-containing feed, the BD-containing feed, and the catalyst composition are contacted in a reaction zone which can be contained in any suitable equipment known to one skilled in the art. One or more pieces of conventional equipment can be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

The reaction temperature is typically maintained within the range of about 80° C. to about 140° C., for example within the range of about 100° C. to about 130° C. Generally, the reaction pressure should be sufficient to maintain the reagents in the liquid state, with such pressure at least, in part, a function of the amount of unreacted BD present in the reaction mixture.

Though the invention is not limited by an upper limit of pressure, for practical purposes the pressure generally ranges from about 15 psia to about 300 psia (about 103 kPa to about 30 2068 kPa).

HCN, substantially free of carbon monoxide, oxygen, ammonia, and water can be introduced to the reaction as a vapor, liquid, or mixtures thereof. As an alternative, cyanohydrins can be used as the source of HCN. See, for example, U.S. Pat. No. 3,655,723.

The molar ratio of the HCN in the feed to the BD in the feed is in the range of about 0.90:1.00 to about 1.04:1.00, for example in the range of about 0.92:1.00 to about 0.98:1.00.

This range of molar ratios can be advantageous over those 40 with a significantly larger excess of BD to HCN in that there can be less unreacted BD to recover and recycle to the process, and yield losses to 2-methylglutaronitrile (MGN) and to BD dimers, oligomers, and related species can be reduced. The molar ratio of the zero-valent nickel in the feed to the BD in the feed is in the range of about 0.00005:1.00 to about 0.0050:1.00, for example in the range about 0.0001: 1.00 to about 0.0010:1.00.

The residence time in the reaction zone (for example, the time necessary for the combined feeds to displace one reactor so volume in a continuous-stirred-tank-reactor (CSTR) is typically determined by the desire to maintain the 2M3BN concentration below about 15 weight percent of the total mass of the reaction mixture, for example at or below about 10 weight percent of the total mass of the reaction mixture, and is also related to the catalyst concentration and reaction temperature. Generally residence times will be in the range of about 0.5 to about 15 hours, for example in the range of about 1 to about 10 hours.

Water can be present in commercially available BD. Water can be undesirable in hydrocyanation processes as it can react with the phosphorus-containing ligand to produce hydrolysis products which are less active or inactive for the desired hydrocyanation and isomerization reactions. The ligand hydrolysis products can also promote undesired side reactions.

Prior to its use in hydrocyanation, BD can be purified to remove impurities such as TBC and water. TBC can be removed from BD by a variety of techniques, for example by distillation or by passing the liquid BD over an absorbent bed such as alumina. Distillation can also be used to remove other impurities, for example 4-vinyl-1-cyclohexene, from BD. Water can be removed from BD by a variety of techniques, for example by passing liquid BD over molecular sieves having a pore size smaller than 10 Angstrom units or by contacting it with alumina.

Lewis Acid Promoter

A reaction for hydrocyanating 3-pentenenitrile to produce adiponitrile preferably takes place in the presence of a promoter for promoting this reaction. The promoter can be a Lewis acid, such as an inorganic compound, an organometallic compound, or combinations thereof, in which a cation of the Lewis acid is selected from the group consisting of scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin. However, the reactions, which take place in the first reaction zone for hydrocyanating 1,3-butadiene and the second reaction zone for isomerizing 2-methyl-3-butenenitrile, preferably take place in the absence or substantial absence of such a promoter.

Dinitriles can be produced in the first reaction zone by the reaction of 3-pentenenitrile (3PN) or 2-methyl-3-butenenitrile (2M3BN) with HCN. Lewis acids are capable of promoting the formation of dinitriles in the first reaction zone. Lewis acids are preferably not introduced into the first reaction zone in detectable amounts. However, a detectable amount of a Lewis acid can be introduced into the first reaction zone, provided that dinitrile formation is minimized. For example, a detectable amount of a Lewis acid can be introduced into the first reaction zone, provided that the amount of dinitriles produced, when none of the Lewis acid is introduced into the first reaction zone, is not increased by more than 5 wt %.

Lewis acid can be unintentionally introduced into the first reaction zone as a result of a unit upset or operator error. However, the continuous production of 3-pentenenitrile can be maintained, provided that the ratio of atomic equivalents of Ni to moles of Lewis Acid in the first reaction zone is less than 10:1 during the course of at least 95% of the production of 3-pentenenitrile.

3-Pentenenitrile produced in the first and second reaction zones can be reacted with hydrogen cyanide to produce dinitriles comprising adiponitrile in a third reaction zone downstream of the first and second reaction zones. A catalyst and a Lewis acid promoter can flow through the third reaction zone along with reactants and products. The reaction temperature is typically maintained within the range of about 25° C. to about 80° C., for example within the range of about 40° C. to about 70° C. Preferably, none of the Lewis acid promoter which flows from the third reaction zone flows into the first reaction zone. However, it is possible that a portion of the Lewis acid promoter which flows from the third reaction zone flows into the first reaction zone, provided that the unwanted production of dinitriles in the first reaction is minimized, as discussed above.

Hydrolysis Catalyst

The hydrolysis catalyst that can be used in practicing a process of the invention is a hydrolysis catalyst of formula (I)

$$(R^{11}X^{11})_n P(OH)_{3-n} \tag{I}$$

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{11}$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring.

$R^{11}$ can be an independently selected (C6-C20)aryl, or (C6-C20)aryl(C1-C10)alkyl, wherein any (C6-C20)aryl or (C6-C20)aryl(C1-C10)alkyl is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring; is directly mutually bonded such that any pair together with the phosphorus atom to which they are bonded, forms a ring.

For example, each independently selected $R^{11}$ can be a group of formula (II)

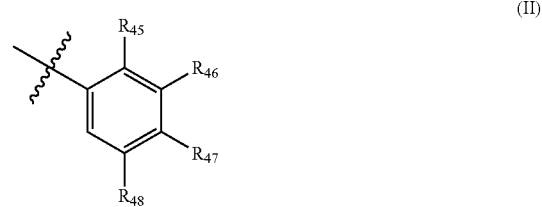

wherein a wavy line indicates a point of attachment; and wherein $R^{45}$ is selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

The hydrolysis catalyst of formula (I) can be a hydrolysis product of at least one of the phosphorus-containing ligand of formula (III), (IIIA), or (IV), produced in a reaction milieu of hydrocyanation of an olefin, or is added to the reaction milieu, or both.

The hydrolysis catalyst therefore can be a compound wherein n is 0 ($H_3PO_3$, phosphorous acid), n=1 (($R^{11}X^{11}$)P (OH)$_2$), a dibasic acid, or n=2 ((R$^{11}$X$^{11}$)$_2$POH), a monobasic acid. The catalyst includes at least one acidic P—O—H group.

It is well known in the art that such phosphorus compounds can be depicted structurally in either trivalent or pentavalent form. The actual compound in question can be viewed as tautomeric isomers, wherein a proton shift from oxygen to phosphorus takes place with rehybridization of the phosphorus-centered electronic orbitals. More specifically, the compound of formula (I), when n=1, or when n=2, can be depicted as shown below in Scheme 1.

Scheme 1:

n=1:

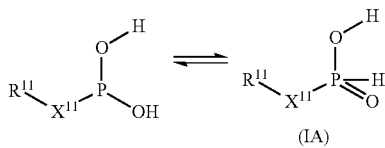

(IA)

n=2

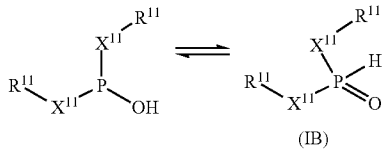

(IB)

As used herein, either trivalent or pentavalent depictions of these structures is intended to indicate either or both forms, whether X$^{11}$ is oxygen or X$^{11}$ is a bond. In formula (IA), when X$^{11}$ is a bond, the compound is termed a phosphonite, when X$^{11}$ is an oxygen, the compound is termed a phosphite monoester. In formula (IB), when both X$^{11}$ groups are each a bond the compound is termed a phosphinite, when both X$^{11}$ groups are each an oxygen, the compound is termed a phosphite diester, and when one X$^{11}$ is a bond and the other X$^{11}$ is an oxygen, the compound is termed a phosphonite, according to common usage. All these subgenera are included within the definition of the hydrolysis catalyst of formula (I), as is phosphorous acid, H$_3$PO$_3$.

Each independently selected R$^{11}$ can be an aryl group, including an unsubstituted aryl group such as phenyl or naphthyl, or a substituted aryl group, e.g., a methyl-substituted aryl group such as tolyl or xylyl. Each independently selected R$^{11}$ group can be a group of formula (II)

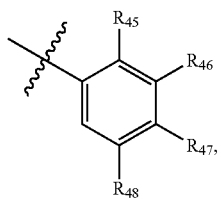

(II)

wherein a wavy line indicates a point of attachment; and wherein R$^{45}$ is selected from the group consisting of (C1-C10)alkyl, (C3-C10)cycloalkyl, (C3-C10)cycloalkyl(C1-C10)alkyl, (C3-C10)cycloalkyl(C1-C10)alkoxyl, (C1-C10)alkoxyl, (C3-C10)cycloalkoxyl, (C3-C10)cycloalkoxyl(C1-C10)alkyl, and (C3-C10)cycloalkoxyl(C1-C10)alkoxyl; and each of R$^{46}$, R$^{47}$ and R$^{48}$ is independently selected from the group consisting of H, (C1-C10)alkyl, (C3-C10)cycloalkyl, (C3-C10)cycloalkyl(C1-C10)alkyl, (C3-C10)cycloalkyl(C1-C10)alkoxyl, (C1-C10)alkoxyl, (C3-C10)cycloalkoxyl, (C3-C10)cycloalkoxyl(C1-C10)alkyl, and (C3-C10)cycloalkoxyl(C1-C10)alkoxyl. A non-hydrogen substituent can be present at only one ortho position of the aryl group, and the other ortho position bears a hydrogen atom.

Accordingly, R$^{45}$, the ortho substituent, is a non-hydrogen substituent, such as an alkyl or alkoxyl group. In an R$^{11}$ group of formula (II), only a single ortho position bears a non-hydrogen substituent, although the meta and para positions can be substituted as described herein. For example, R$^{45}$ can be methyl, ethyl or isopropyl, or can be methoxyl, ethoxyl, or isopropoxyl. For example, all of R$^{46}$, R$^{47}$ and R$^{48}$ can be H. For example R$^{47}$, the para substituent, can also be an alkyl or alkoxyl group, such as methyl or methoxyl. More specifically, the group of formula (II) can be a 2,4-xylyl group, i.e., wherein R$^{45}$ and R$^{47}$ are each methyl, and R$^{46}$ and R$^{48}$ are each hydrogen. For example, for the catalyst of formula (I), each X$^{11}$ can be oxygen and each R$^{11}$ can be a phenyl group, a tolyl group, or a xylyl group.

The hydrolysis catalyst can be of formula (IA1):

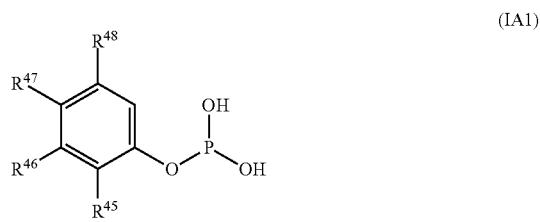

(IA1)

or can be of formula (IB1):

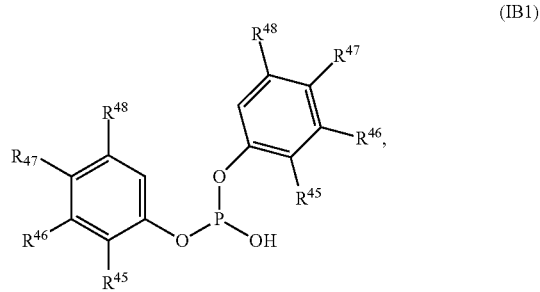

(IB1)

or is a mixture thereof;

wherein R$^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of R$^{46}$, R$^{47}$ and R$^{48}$ is independently selected from the group consisting of H (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

For example, for the hydrolysis catalyst of formula (IA1), (IB1), or both, R$^{45}$ can be methyl, ethyl or isopropyl; additionally, R$^{46}$ can be hydrogen, and R$^{47}$ and R$^{48}$ can be independently selected from H or methyl. The ortho position of the phenyl ring not bearing R$^{45}$ bears a hydrogen atom.

More specifically, the hydrolysis catalyst can be of formula (IA2):

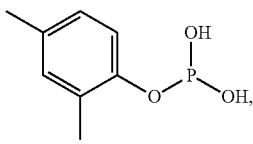
(IA2)

or can be of formula (IB2):

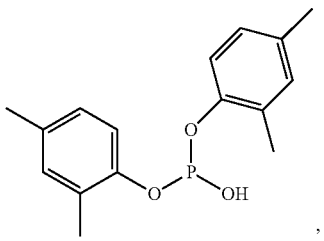
(IB2)

or can be a mixture thereof.

The hydrolysis catalyst of formula (I) can be produced in the presence of water in a reaction mixture containing phosphorus-based compounds having at least one phosphite ester bond, useful as ligands for catalytic transition metal complexes, or can be added to the phosphite ester ligand blend, or both. The production of the catalyst can take place in a hydrocyanation reaction milieu comprising the ligand blend, a transition metal such as nickel, water, and at least one organic component. For example, the organic component can comprise pentenenitrile, such as 3-pentenenitrile, produced by hydrocyanation of butadiene, or adiponitrile, produced by hydrocyanation of pentenenitrile. Thus, at least a portion of the hydrolysis catalyst can itself be a hydrolytic degradation product of the phosphorus-based ligand during hydrocyanation of an alkene in the presence of even trace or controlled amounts of water. Additional hydrolysis catalyst can be deliberately added to bring about hydrolysis of one or more of the components of the ligand blend, such as selective hydrolysis of a monodentate ligand, e.g., of formula (IV), in the presence of a bidentate ligand, e.g., of formula (III) or a tridentate ligand, e.g., of formula (IIIA) in a ligand blend comprising ligands of both formula (III) and/or formula (IIIA), and formula (IV).

Phosphorus-Based Ligand

A phosphorus-based ligand subject to hydrolysis (i.e., containing at least one phosphite ester bond), the hydrolysis of which can be catalyzed by the hydrolysis catalyst of formula (I) in carrying out a process of the present invention, can be a component of a hydrocyanation catalyst, such as when combined with a transition metal such as nickel, as known in the art. The ligand can be, for example, a phosphite, a phosphonite, a phosphinite, a phosphine, or a mixed phosphorus-based ligand or a combination of such members, provided the ligand contains at least one hydrolyzable P—O—C bond, wherein P is a phosphorus atom (which additionally bears other substituents), O is an oxygen atom, and C represent an organic radical, such as an aryl group.

The phosphorus-based ligand can be monodentate or multidentate, for example, bidentate or tridentate. The term "monodentate" is well known in the art, and means that each molecule of the ligand possesses a single phosphorus atom (e.g., a compound of formula (IV)), which can be bonded to a single metal atom. The term "bidentate" is well known in the art, and means that each molecule of the ligand possesses two phosphorus atoms (e.g., a compound of formula (III)), and both phosphorus atoms of the ligand can be bonded to a single metal atom. The term "tridentate" means that each molecule of the ligand possesses three phosphorus atoms (e.g., a compound of formula (IIIA)), and all three phosphorus atoms on the ligand can be bonded to a single metal atom. The terms "bidentate" and "tridentate" are also known in the art as chelate ligands.

As used herein, the term "mixed phosphorus-based ligand" means a phosphorus-based ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members, provided that there is at least one P—O—C bond, wherein P is a phosphorus atom, O is an oxygen atom, and C represent an organic radical, such as an aryl group, that is subject to hydrolysis under acid catalysis.

The hydrolysis catalyst of formula (I) as can be used in practice of a process of the invention can be derived from hydrolysis of a phosphorus-based ligand, such as by hydrolysis of a monodentate phosphorus-based ligand. This hydrolysis can occur under the conditions present in a hydrocyanation reaction milieu, in the presence of even a trace or controlled amount of water, to generate the hydrolysis catalyst.

Suitable phosphorus-based ligands for the transition metal, e.g., nickel, complex, can be selected from the group consisting of compounds of formula (III), formula (IIIA), and formula (IV), or combinations thereof.

Bidentate and tridentate ligands can be of formulas (III) and (IIIA), respectively, thus including a bidentate phosphorus-based ligand of formula (III)

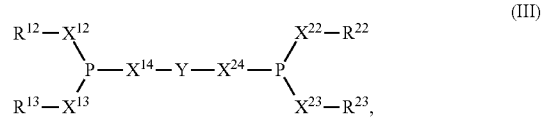
(III)

a tridentate phosphorus-based ligand of formula (IIIA)

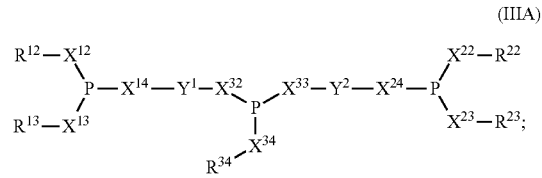
(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

$X^{12}$, $X^{13}$, $X^{14}$, $X^{22}$, $X^{23}$, $X^{24}$, $X^{32}$, $X^{33}$, and $X^{34}$, can each be oxygen. In such a case, e.g., for formula (III) or (IIIA), the bridging group Y, $Y^1$, and/or $Y^2$ is bonded to phosphite groups. Or, $X^{12}$ and $X^{13}$ can each be oxygen and $X^{14}$ a single bond, or $X^{12}$ and $X^{13}$ each a oxygen and $X^{14}$ a single bond. And, $X^{22}$, $X^{23}$ and $X^{24}$ can each be oxygen, or $X^{22}$ and $X^{24}$ can each be oxygen and $X^{23}$ a single bond, or $X^{22}$ and $X^{23}$ can each be oxygen and $X^{24}$ a single bond, or $X^{23}$ can be oxygen and $X^{22}$ and $X^{24}$ each a single bond, and so forth. Each phosphorus atom of in a compound of formula (III), (IIIA), or (IV), can be the central atom of a phosphite, phosphonite, phosphinate, phosphinite or phosphine, preferably a phosphonite or a phosphite.

However, at least one of the X groups of each of formulas (III), (IIIA), and (IV) is an oxygen atom, providing a P—O—C bond that is subject to hydrolysis under acidic conditions, wherein P is a phosphorus atom, O is an oxygen atom, and C represent an organic radical, such as an aryl group. The bridging group Y, $Y^1$, or $Y^2$ can each independently be a (C6-C20)arylene group, each ring of which is unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalky(C1-C10)alkoxy 1, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl; in particular, Y, Y', and/or $Y^2$ can, combined with the X groups to which it is bonded, be a pyrocatechol, a bis(phenol) or bis(naphthol). By an "arylene" group is meant a bifunctional group comprising one or more (C6-C20)aryl rings, each ring of which can be unsubstituted, or substituted, e.g., with 1-4 independently selected (C1-C10)alkyl, (C3-C10)cycloalkyl, (C3-C10)cycloalkyl(C1-C10)alkyl, (C3-C10)cycloalkyl(C1-C10)alkoxyl, (C1-C10)alkoxyl, (C3-C10)cycloalkoxyl, (C3-C10)cycloalkoxyl(C1-C10) alkyl, and (C3-C10)cycloalkoxyl(C1-C10)alkoxyl, (C6-C20)aryl, (C6-C20)aryl(C1-C10)alkyl, halogen, such as fluorine, chlorine, bromine; halogenated alkyl, such as trifluoromethyl; aryl, such as phenyl or other unsubstituted or substituted aryl groups.

In any of the ligands of formulas (III) or (IIIA), i.e., the bidentate and tridentate ligands, respectively, the R groups can be as described herein; for example, for formula (III), $R^{12}$, $R^{13}$, $R^{22}$, $R^{23}$, and for the ligand of formula (IIIA), $R^{12}$, $R^{13}$, $R^{22}$, $R^{23}$, and $R^{34}$, each independently is (C1-C10) alkyl, (C3-C10)cycloalkyl, ((C3-C10)cycloalkyl C1-C10) alkyl, (C6-C20)aryl, or (C6-C20)aryl(C1-C10)alkyl, wherein for any (C6-C20)aryl or (C6-C20)aryl(C1-C10) alkyl, each ring thereof is unsubstituted or is substituted with 1-4 substituents independently selected from the group consisting of (C1-C10)alkyl, (C3-C10)cycloalkyl, (C1-C10) alkoxy, (C3-C10)cycloalkoxy, (C3-C10)cycloalkyl(C1-C10)alkyl, (C3-C10)cycloalkoxy(C1-C10)alkyl, (C3-C10) cycloalkyl(C1-C10)alkoxy, (C3-C10)cycloalkoxy(C1-C10) alkoxy, (C6-C20)aryl, and (C6-C20)aryl(C1-C10)alkyl; or, optionally, $R^{12}$ and $R^{13}$ are mutually directly bonded, or $R^{22}$ and $R^{23}$ are mutually directly bonded, or both, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a ring.

The R groups of formulas (III) and (IIIA) can be aryl radicals, preferably those having from 6 to 20 carbon atoms, which can be unsubstituted or mono- or polysubstituted, in particular by (C1-C10)alkyl, (C3-C10)cycloalkyl, (C3-C10) cycloalkyl(C1-C10)alkyl, (C3-C10)cycloalkyl(C1-C10) alkoxyl, (C1-C10)alkoxyl, (C3-C10)cycloalkoxyl, (C3-C10)cycloalkoxyl(C1-C10)alkyl, and cycloalkoxyl(C1-C10)alkoxyl. The $R^{12}$ and $R^{13}$ groups can each be separate or bridged. The $R^{22}$ and $R^{23}$ groups can also each be separate or bridged. The $R^{12}$, $R^{13}$, $R^{22}$ and $R^{23}$ radicals can each be separate, one pair can be bridged and one pair separate, or both pairs can be bridged, in the manner described.

The monodentate ligand of formula (IV) can be a monodentate phosphorus-based ligand of formula (IV)

$$P(X^1R^1)(X^2R^2)(X^3R^3) \qquad (IV)$$

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10) alkyl, (C3-C10)cycloalkyl, (C3-C10)cycloalkyl(C1-C10) alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$, each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring. The ligand of formula (IV) can be a phosphite, a phosphonite, a phosphinite, and the like, provided that at least one phosphite ester bond, e.g., a P—O—C bond, subject to acid-catalyzed hydrolysis, is present in the ligand.

$R^1$, $R^2$ and $R^3$ can independently alkyl, cycloalkyl, alkoxy, or cycloalkyoxy radicals, the alkyl radicals preferably having from 1 to 10 carbon atoms, such as methyl, ethyl, n-propyl, i-propyl, n-butyl, i-butyl, s-butyl, t-butyl, and the cycloalkyl radical preferably having from 3 to 10 carbon atoms, such as cyclopropyl, cyclobutyl, cyclpentyl, and cyclohexyl; aryl groups such as phenyl, o-tolyl, m-tolyl, p-tolyl, 1-naphthyl, or 2-naphthyl, preferably having from 6 to 20 carbon atoms, such as 1,1'-biphenyl, 1,1'-binaphthyl. The $R^1$, $R^2$ and $R^3$ groups can be bonded together directly, i.e. not solely via the central phosphorus atom. $R^1$, $R^2$ and $R^3$ groups can be selected from the group consisting of phenyl, o-tolyl, m-tolyl and p-tolyl. Or, two of the $R^1$, $R^2$ and $R^3$ groups can be phenyl groups. Or, two of the $R^1$, $R^2$ and $R^3$ groups can be o-tolyl groups. Alternatively, any or all of the $R^1$, $R^2$ and $R^3$ groups can be xylyl, such as 2,4-xylyl.

Particular compounds which can be used are those of the formula (IVa) below:

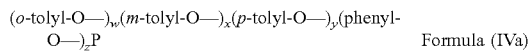

Formula (IVa)

where w, x, y, z are each a natural number and the following conditions apply: w+x+y+z=3 and z=less than or equal to 2.

Examples of such compounds (IVa) include: (o-tolyl-O—)$_3$P, (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

An example of a bidentate phosphite ligand that is useful in the inventive processese, i.e., a compound of formula (III), above, is a ligand having formula (V), shown below

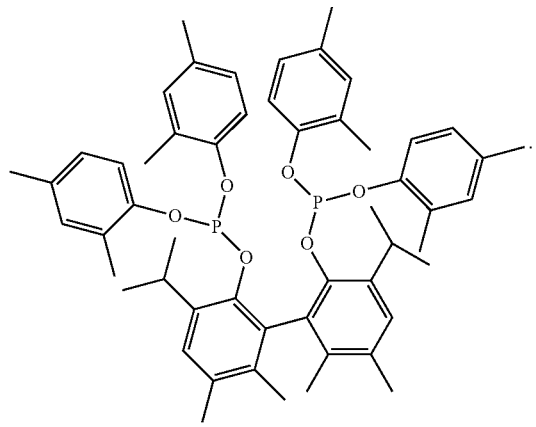

(V)

For the ligand of formula (V), all substituents of the two covalently mutually bonded phosphite esters are substituted aryl groups, bearing alkyl substituent.

Further examples of bidentate phosphite ligands that are useful in the inventive processes include those having the formulae (VI) to (IX), shown below wherein for each formula, $R^{17}$ can selected from the group consisting of methyl, ethyl, and isopropyl, and $R^{18}$ and $R^{19}$ can be independently selected from H and methyl. Or, each of $R^{17}$, $R^{18}$, and $R^{19}$ can be independently higher alkyls, or cycloalkyls, alkoxyls, or cycloalkoxyls.

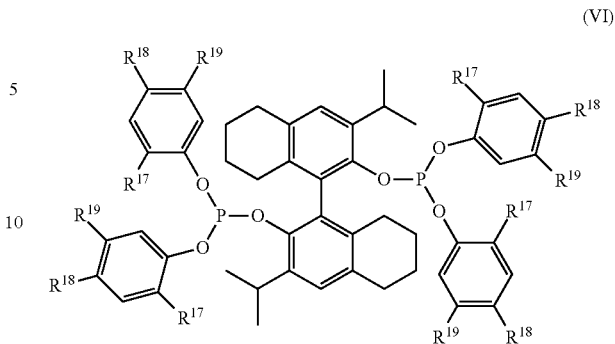

(VI)

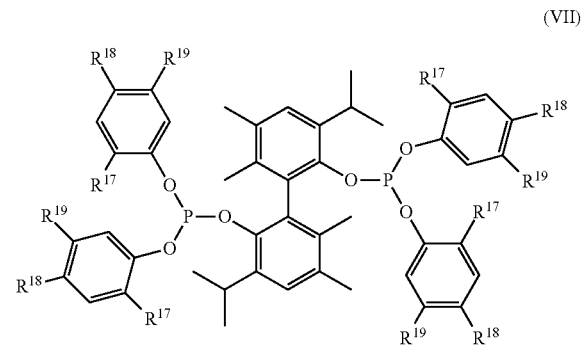

(VII)

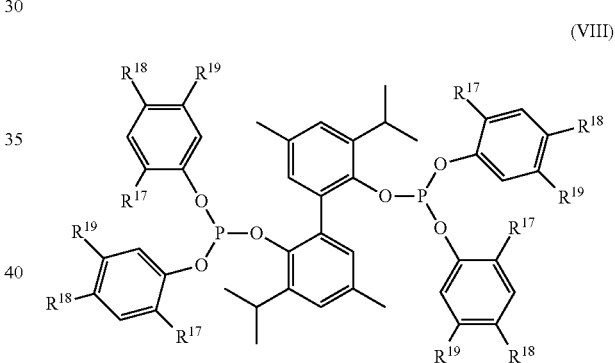

(VIII)

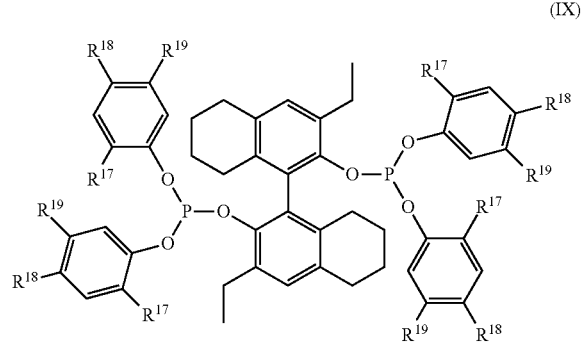

(IX)

Additional examples of bidentate phosphite ligands that are useful in the inventive processes include a ligand selected from a member of the group represented by formulae (X) and (XI), in which all like reference characters can have the same meaning, or can be independently selected.

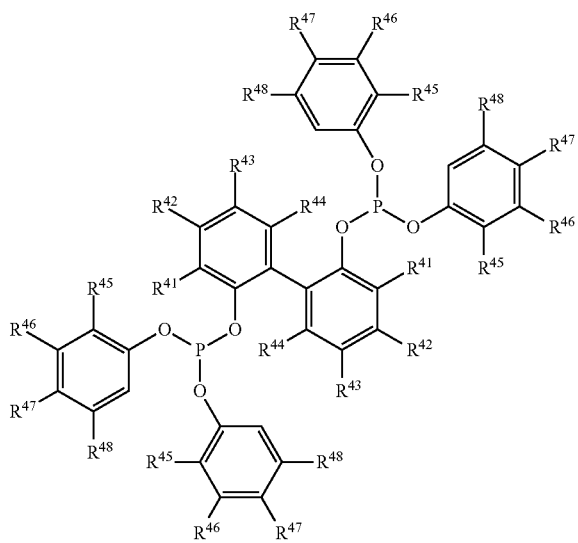

(X)

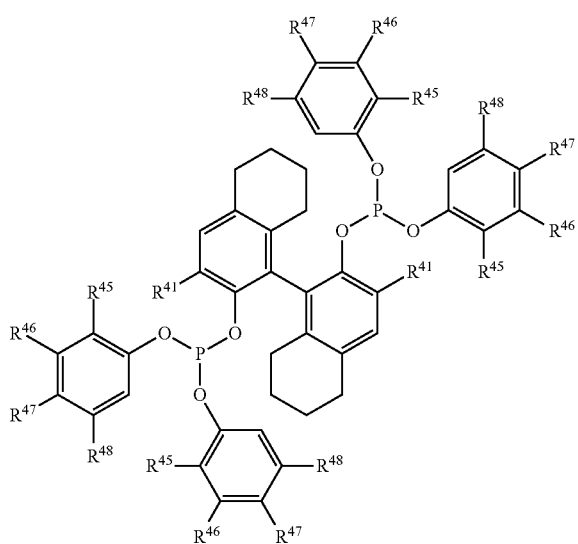

(XI)

wherein, each $R^{41}$ and $R^{45}$ can be independently selected from the group consisting of (C1-C10)alkyl, (C3-C10)cycloalkyl, (C1-C10)alkoxyl, and (C3-C10)cycloalkoxyl, and each of $R^{42}$, $R^{43}$, $R^{44}$, $R^{46}$, $R^{47}$ and $R^{48}$ is independently selected from the group consisting of H, (C1-C10)alkyl, and (C3-C10) cycloalkyl.

For example, the bidentate phosphite ligand can be selected from a member of the group represented by formula (X) and formula (XI), wherein:
$R^{41}$ is methyl, ethyl, isopropyl, or cyclopentyl;
$R^{42}$ is H or methyl;
$R^{43}$ is H, (C1-C10)alkyl, (C3-C10)cycloalkyl, (C1-C10)alkoxyl, or (C3-C10)cycloalkoxyl;
$R^{44}$ is H or methyl;
$R^{45}$ is methyl, ethyl, or isopropyl; and
$R^{46}$, $R^{47}$ and $R^{48}$ are independently selected from the group consisting of H, (C1-C10)alkyl, (C3-C10)cycloalkyl, (C1-C10)alkoxyl, and (C3-C10)cycloalkoxyl.

As additional examples, the bidentate phosphite ligand can be selected from a member of the group represented by formula (X), wherein:

$R^{41}$, $R^{44}$, and $R^{45}$ are methyl;
$R^{42}$, $R^{46}$, $R^{47}$ and $R^{48}$ are H; and
$R^{43}$ is (C1-C10)alkyl, (C3-C10)cycloalkyl, (C1-C10)alkoxyl, or (C3-C10)cycloalkoxyl;
or wherein:
$R^{41}$ is isopropyl;
$R^{42}$ is H;
$R^{43}$ is (C1-C10)alkyl, (C3-C10)cycloalkyl, (C1-C10)alkoxyl, or (C3-C10)cycloalkoxyl;
$R^{44}$ is H or methyl;
$R^{45}$ is methyl or ethyl;
$R^{46}$ and $R^{48}$ are H or methyl; and
$R^{47}$ is H, methyl, or tertiary-butyl;
or the bidentate phosphite ligand can be selected from a member of the group represented by formula XI, wherein:
$R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand can be represented by Formula (X), wherein $R^{41}$ is isopropyl; $R^{42}$, $R^{46}$, and $R^{48}$ are H; and $R^{43}$, $R^{44}$, $R^{45}$, and $R^{47}$ are methyl.

As another example, the ligand of formula (III) is of formula (XII)

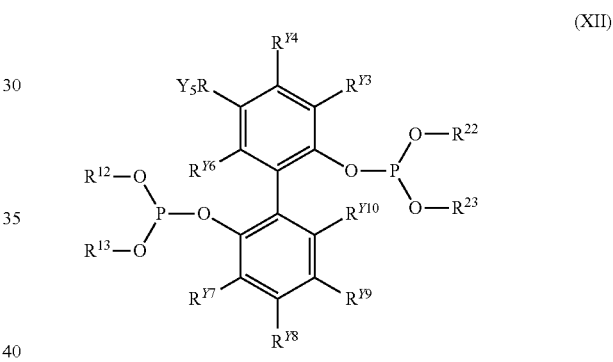

(XII)

wherein $R^{12}$, $R^{13}$, $R^{22}$ and $R^{23}$ are each independently an unsubstituted or a substituted monovalent aryl, and each of $R^{Y3}$—$R^{Y10}$ is independently selected from the group consisting of hydrogen, (C1-C10)alkyl, and (C1-C10)alkoxy, or wherein two adjacent $R^{Y3}$—$R^{Y10}$ groups together form an optionally substituted fused aryl ring.

More specifically, the invention can provide a process wherein, for the ligand of formula (XII), $R^{12}$, $R^{13}$, $R^{22}$, and $R^{23}$ are each independently phenyl substituted at a respective first ortho-position with a (C1-C10)alkyl or (C1-C10)alkoxy, at a respective second ortho-position with hydrogen, and wherein respective meta- and para-positions of the $R^{12}$, $R^{13}$, $R^{22}$, and $R^{23}$ phenyls can each independently be unsubstituted or be independently substituted with 1-3 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;
$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

It will be recognized that formulae (V) to (XII) are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, binaphthyl, or biphenyl bridging groups of formulae (V) to (XII), respectively, can bring the two phosphorus atoms of each bidentate ligand in closer proximity to one another and can allow the phosphite ligand to bind to nickel in a bidentate fashion. In addition, use of an optically active moiety such as sec-butyl for $R^{41}$ can result in optically active catalysts.

Particular blends for the process of the present invention are those which contain the ligand of the formula (V), above, and phosphite triesters of the following formulae (XIII) and (XIV):

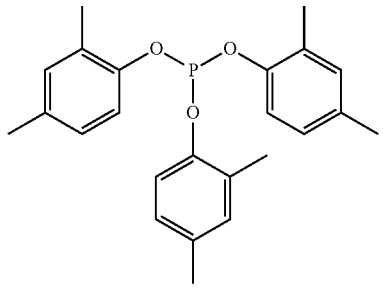

(XIII)

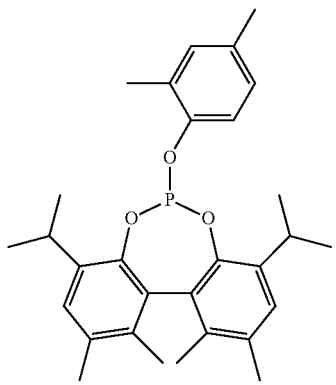

(XIV)

Accordingly, the invention can provide a process of hydrolyzing a phosphorus-based ligand for a transition metal catalyst, wherein the ligand comprises at least one phosphite ester group; the process comprising:
i) contacting a hydrolysis catalyst of formula (I)

$$(R^{11}X^{11})_nP(OH)_{3-n} \quad (I)$$

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein any (C6-C20)aryl or (C6-C20)aryl(C1-C10)alkyl is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring;

with one or more phosphorus-based ligand selected from the group consisting of:

a bidentate phosphorus-based ligand of formula (III)

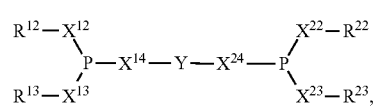

(III)

a tridentate phosphorus-based ligand of formula (IIIA)

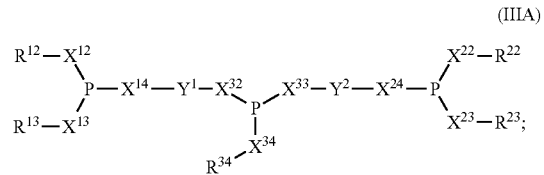

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein any (C6-C20)aryl or (C6-C20)aryl(C1-C10)alkyl of $R^{12}$, $R^{13}$, $R^{22}$, $R^{23}$, or $R^{34}$, is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;
and a monodentate phosphorus-based ligand of formula (IV)

$$P(X^1R^1)(X^2R^2)(X^3R^3) \quad (IV)$$

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)

alkyl of $R^1$, $R^2$, or $R^3$, each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring; and a mixture thereof;

in the presence of water and, optionally, one or more organic liquids, under conditions of time, temperature, and concentration sufficient to bring about hydrolysis of the at least one phosphite ester bond to provide a hydrolysis product; and ii) separating the hydrolysis catalyst and the hydrolysis product from the ligand by liquid-liquid extraction.

$R^1$, $R^2$, $R^3$, $R^{11}$, $R^{12}$, $R^{13}$, $R^{22}$, $R^{23}$ or $R^{34}$ can each be an independently selected (C6-C20)aryl group, which is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy (C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or wherein one or more pair of $R^1$ and $R^2$, or $R^{12}$ and $R^{13}$, or $R^{22}$ and $R^{23}$, or when n=2, two $R^{11}$, is directly mutually bonded such that any pair together with the respective $X^1$, $X^2$, $X^{11}$, $X^{12}$, $X^{13}$, $X^{22}$ or $X^{23}$ groups and the phosphorus atom to which they are bonded, forms a ring.

Each independently selected $R^1$, $R^2$, $R^3$, $R^{11}$, $R^{12}$, $R^{13}$, $R^{22}$, $R^{23}$ or $R^{34}$ can be a group of formula (II)

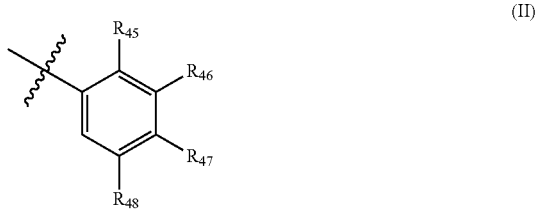
(II)

wherein a wavy line indicates a point of attachment; and wherein $R^{45}$ is selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

Y (in formula (III)), or independently selected $Y^1$ or $Y^2$ (in formula (IIIA)), can be a (C6-C20)arylene group, wherein each ring thereof is independently unsubstituted or is independently substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl (C1-C10)alkyl, fluorine, chlorine, bromine, or (C1-C10)haloalkyl.

In reference to the hydrolysis catalyst of formula (I), the hydrolysis catalyst of formula (I) can a hydrolysis product of at least one of the phosphorus-containing ligand of formula (III), (IIIA), or (IV), produced in a reaction milieu of hydrocyanation of an olefin, or is added to the reaction milieu, or both. In particular, the hydrolysis catalyst of formula (I) can itself be a hydrolysis product of a monodentate ligand of formula (IV). In a hydrocyanation reaction medium or milieu, the phosphorus-based ligand blend, the metal, and even a trace or controlled amount of water, or a larger quantity of water, can be present in a reaction wherein, e.g., butadiene and hydrogen cyanide are present. An organic component, such as a reaction product, e.g., pentenenitriles (which can be a mix of pentenenitrile isomers such as 2-, 3-, and 4-pentenenitrile) can be present. Adiponitrile can also be present. Additional components such as solvents, diluents, and the like, can also be present. Also, reaction adjuvants such as metal salts (e.g., $ZnCl_2$ and the like), for example, as co-catalysts and the like, can be present.

The ligand blend used in the hydrocyanation reaction can be monitored and its contents adjusted as needed. For example, in ligand blends wherein the hydrolysis catalyst brings about selective hydrolysis of a monodentate ligand in the presence of a bidentate and/or tridentate ligand, the hydrolyzed monodentate ligand product, an acid phosphite ligand hydrolysis or decomposition product, can be removed for the ligand pool, along with any acidic hydrolysis catalyst, by an extraction step. For example, a stream of ligand pool material can be processed through a side-process during execution of the main hydrocyanation reaction in a fluidized bed reaction vessel, or other suitable reaction apparatus, for adjustment of concentrations and relative abundances of various ligand blend components. This separation of acidic ligand hydrolysis products produced by action of the hydrolysis catalyst of formula (I), along with the acidic catalyst itself, can be carried out by an extraction process. For example, the removal step ii) can through extraction between a nonpolar and a polar organic solvent. The nonpolar solvent can comprise cyclohexane. The polar solvent can be a raffinate from the hydrocyanation reaction of butadiene, comprises adiponitrile, or both. By a "raffinate" is meant the composition from which the unwanted components have been removed or extracted, i.e., "that which has been refined."

Specific bidentate phosphorus-based ligands that can be used in the processes of the invention include the ligand of formula (III) is of formula (X):

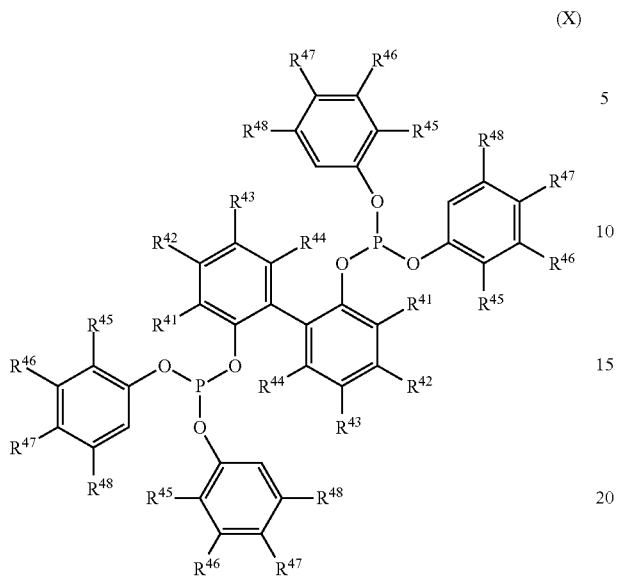

(X)

wherein each $R^{41}$ and $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

For example, for a ligand of formula (X),
$R^{41}$ can be methyl, ethyl, isopropyl, or cyclopentyl;
$R^{42}$ can be H or methyl;
$R^{43}$ can be H or (C1-C4)alkyl;
$R^{44}$ can be H or methyl;
$R^{45}$ can be methyl, ethyl, or isopropyl; and
$R^{46}$, $R^{47}$ and $R^{48}$ can be independently H or (C1-C4)alkyl.

Bidentate phosphorus-based ligands that can be used in the processes of the invention include a ligand of formula (III) that is of formula (VII):

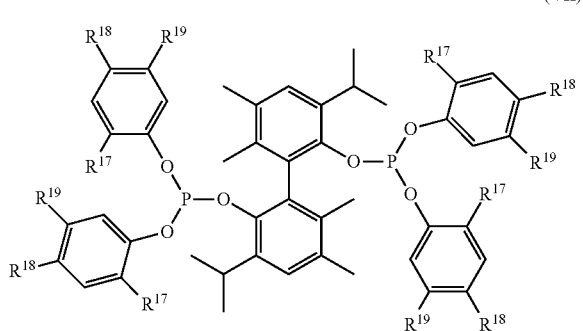

(VII)

wherein each $R^{17}$ is independently methyl, ethyl, or isopropyl, and $R^{18}$ and $R^{19}$ are independently H or methyl.

A specific bidentate phosphorus-based ligand of formula (III) that can be used in the processes of the invention is a ligand of formula (V):

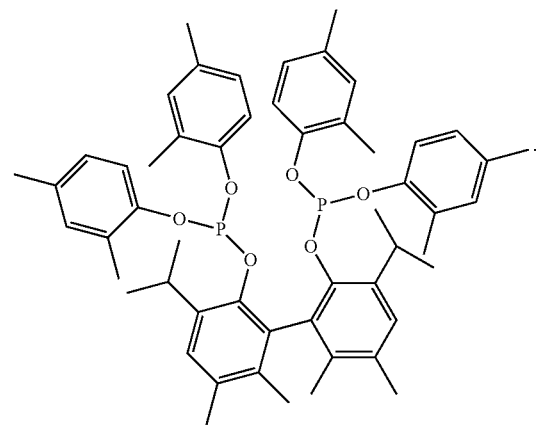

(V)

Specific bidentate phosphorus-based ligands that can be used in the processes of the invention can include the ligand of formula (III) is of formula (XII)

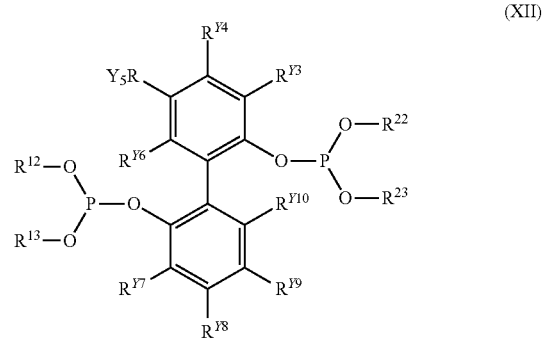

(XII)

wherein $R^{12}$, $R^{13}$, $R^{22}$ and $R^{23}$ are each independently an unsubstituted or a substituted monovalent aryl, and each of $R^{Y3}$—$R^{Y10}$ is independently selected from the group consisting of hydrogen, (C1-C10) alkyl, and (C1-C10)alkoxy, or wherein two adjacent $R^{Y3}$—$R^{Y10}$ groups together form an optionally substituted fused aryl ring.

More specifically, the invention can provide processes wherein for the ligand of formula (XII), $R^{12}$, $R^{13}$, $R^{22}$, and $R^{23}$ are each independently phenyl substituted at a respective first ortho-position with a (C1-C10)alkyl or (C1-C10)alkoxy, at a respective second ortho-position with hydrogen, and wherein respective meta- and para-positions of the $R^{12}$, $R^{13}$, $R^{22}$, and $R^{23}$ phenyls can each independently be unsubstituted or be independently substituted with 1-3 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

In carrying out processes of the invention, as disclosed and claimed herein, the hydrolysis catalyst can be of formula (IA1):

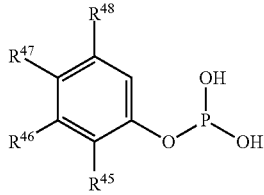

(IA1)

or is of formula (IB1):

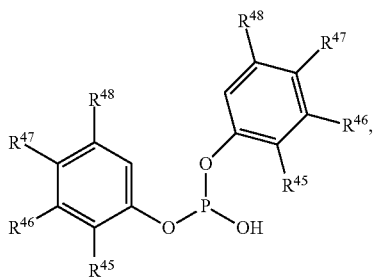

(IB1)

or is a mixture thereof;

wherein $R^{45}$ is selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

For example, in the hydrolysis catalyst of formula (IA1), (IB1), or both, $R^{45}$ can be methyl, ethyl, or isopropyl; and more specifically, in the hydrolysis catalyst of formula (IA1), (IB1), or both, $R^{45}$ can be methyl, ethyl, or isopropyl, $R^{46}$ can be hydrogen, and $R^{47}$ and $R^{48}$ can be independently selected from H and methyl.

Even more specifically, the hydrolysis catalyst can have the following formula (IA2):

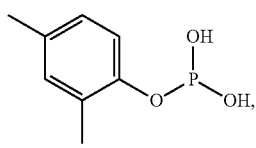

(IA2)

or can be of formula (IB2):

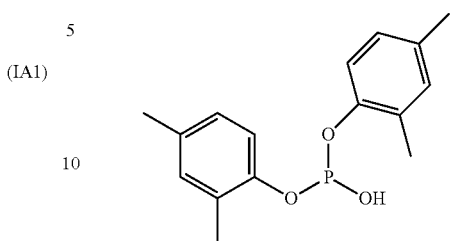

(IB2)

or can be a mixture thereof.

These hydrolysis catalysts can arise in situ in a hydrocyanation reaction milieu through hydrolysis of a phosphite ester bond of tris(2,4-xylyl)phosphite (formula (XIII), a monodentate ligand of formula (IV).

All the examples of hydrolysis catalysts, monodentate phosphorus-based ligands, and bidentate/tridentate phosphorus-based ligands as described above can also be used in carrying out the below-described processes of the invention. For the sake of brevity, they are not recapitulated in the description below, but it is apparent that analogous examples are disclosed and claimed herein.

The invention can provide a process for modifying the relative ratio of two phosphorus-based ligands for a transition metal catalyst, wherein each ligand in the blend comprises at least one phosphite ester group, in a ligand blend comprising at least two phosphorus-based ligands, a first component of the blend being selected from the group consisting of a bidendate phosphorus-based ligand of formula (III) and a tridentate phosphorus-based ligand of formula (IIIA):

a bidentate phosphorus-based ligand of formula (III)

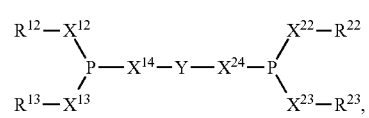

(III)

a tridentate phosphorus-based ligand of formula (IIIA)

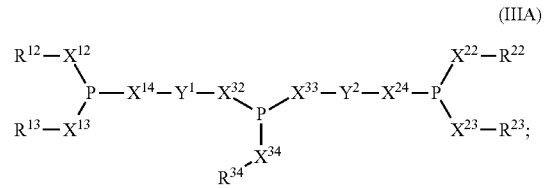

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein any (C6-C20)aryl or (C6-C20)aryl(C1-C10)alkyl of $R^{12}$, $R^{13}$, $R^{22}$, $R^{23}$, or $R^{34}$, is unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

and, a second component of the blend being a monodentate phosphorus-based ligand of formula (IV)

$$P(X^1R^1)(X^2R^2)(X^3R^3) \quad (IV)$$

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10) alkyl, (C3-C10)cycloalkyl, (C3-C10)cycloalkyl(C1-C10) alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$, each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring; the process comprising:

i) selectively hydrolyzing a phosphite ester group of the second component of the ligand blend with respect to a phosphite ester group of the first component of the ligand blend, by contacting the blend with a hydrolysis catalyst of formula (I)

$$(R^{11}X^{11})_nP(OH)_{3-n} \quad (I)$$

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl (C1-C10)alkyl, (C6-C20)aryl, or (C6-C20)aryl(C1-C10) alkyl, wherein for any (C6-C20)aryl or (C6-C20)aryl(C1-C10)alkyl of $R^{11}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10) cycloalkyl(C1-C10)alkyl, (C3-C10)cycloalkoxy(C1-C10) alkyl, (C3-C10)cycloalkyl(C1-C10)alkoxy, (C3-C10) cycloalkoxy(C1-C10)alkoxy, (C6-C20)aryl, and (C6-C20) aryl(C1-C10)alkyl; or, when n=2, two $R^{11}$ groups are optionally directly bonded to each other such that the two $R^{11}X^{11}$ groups, together with the phosphorus atom to which they are bonded, form a ring;

in the presence of water and, optionally, one or more organic liquids, under conditions of time, temperature, and concentration sufficient to bring about hydrolysis of the at least one phosphite ester bond of the second component to provide a hydrolysis product, and ii) separating the hydrolysis catalyst and the hydrolysis product from the ligand blend by liquid-liquid extraction.

In carrying out the above-described inventive process, the hydrolysis catalyst of formula (I) can be a hydrolysis product of at least one of the phosphorus-containing ligand of formula (III), (IIIA), or (IV), produced in a reaction milieu of hydrocyanation of an olefin, or is added to the reaction milieu, or both. More specifically, the hydrolysis catalyst of formula (I) can be a hydrolysis product of the monodentate ligand of formula (IV). However, it can also arise by hydrolysis of a bidentate ligand of formula (III) or a tridentate ligand of formula (IIIA).

Again, the ligand degradation products (hydrolysis products) of a ligand type that is selectively hydrolyzed under the reaction conditions in the presence of the hydrolysis catalyst (which can be auto-generated in the reaction milieu, deliberately added, or both) can be separated from the ligand blend, such as, e.g., wherein the removal step ii) is through extraction between a nonpolar and a polar organic solvent. As described above, the nonpolar solvent can comprise cyclohexane, or similar nonpolar solvents, or mixtures thereof. As described above, polar solvent can be a raffinate that arises from the extraction process as applied to the reaction milieu resulting from the hydrocyanation reaction of butadiene, comprises adiponitrile, or both. For example, the process stream undergoing purification or adjustment of ligand contents can be extracted with a non-polar solvent, partitioned versus a liquid medium containing the ligand blend, which in the extraction process becomes the raffinate of that extraction.

The components of the ligand blend can be any as described above for phosphorus-based ligands of formulas (III), (IIIA), and (IV). Similarly the hydrolysis catalyst of formula (I) can be any described above.

More specifically, the bidentate ligand can be of formula (V),

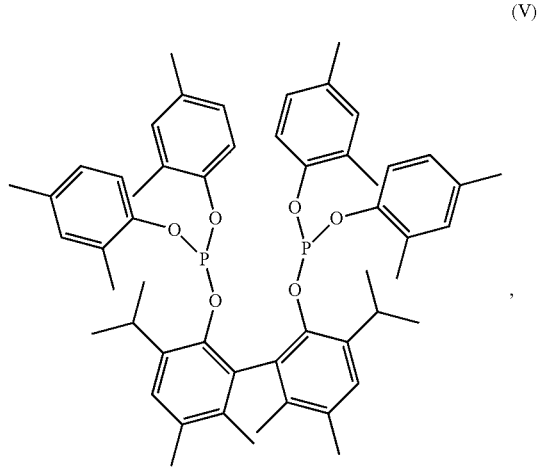

the monodentate ligand can be of formula (XIII)

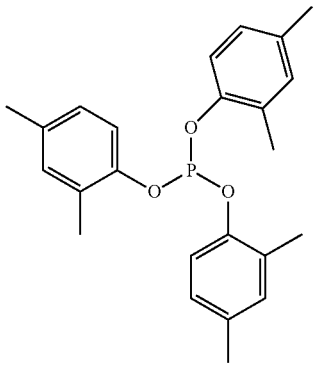
(XIII)

or can be of formula (XIV):

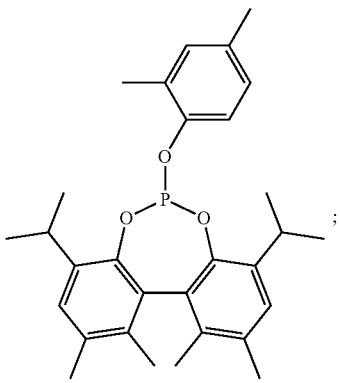
(XIV)

or a mixture thereof,
and the hydrolysis catalyst can be of the formula (IA2):

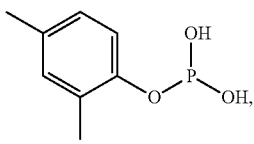
(IA2)

or of formula (IB2):

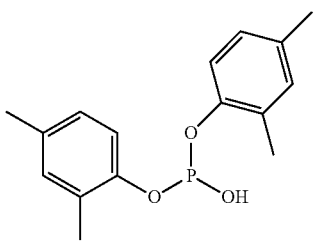
(IB2)

or can be a mixture thereof.

The reaction milieu can include cyclohexane and/or toluene, and can also include one or more nitriles, such as pentenenitriles (e.g., 3-pentenenitrile), adiponitrile, or a mixture thereof.

The invention can provide a process for maintaining a concentration of a phosphorus-based bidentate ligand or of a phosphorus-based tridentate ligand, or both, within a concentration range, in a phosphorus-based ligand blend further comprising a monodentate phosphorus-based ligand, for a transition metal catalytic complex in a hydrocyanation reaction milieu comprising water and at least one organic liquid, wherein each phosphorus-based ligand in the blend comprises at least one phosphite ester group, the ligand blend comprising at least two phosphorus-based ligands, a first component of the ligand blend being a bidendate phosphorus-based ligand of formula (III) and/or a tridentate phosphorus-based ligand of formula (IIIA):

a bidentate phosphorus-based ligand of formula (III)

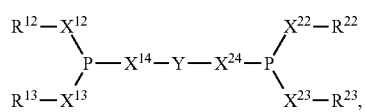
(III)

a tridentate phosphorus-based ligand of formula (IIIA)

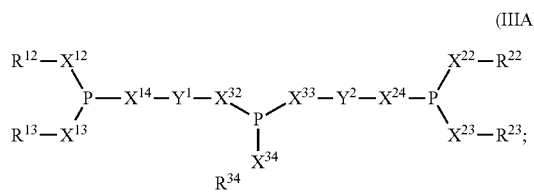
(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;
and,
a second component of the blend being a ligand comprising a monodentate phosphorus-based ligand of formula (IV)

$$P(X^1R^1)(X^2R^2)(X^3R^3) \tag{IV}$$

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10) alkyl, (C3-C10)cycloalkyl, (C3-C10)cycloalkyl(C1-C10) alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$, each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;
the process comprising:
i) contacting the ligand blend in the hydrocyanation reaction milieu with a hydrolysis catalyst of formula (I)

$$(R^{11}X^{11})_nP(OH)_{3-n} \tag{I}$$

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl (C1-C10)alkyl, (C6-C20)aryl, or (C6-C20)aryl(C1-C10) alkyl, wherein for any (C6-C20)aryl or (C6-C20)aryl(C1-C10)alkyl each ring thereof is unsubstituted or is substituted with 1-4 substituents independently selected from the group consisting of (C1-C10)alkyl, (C3-C10)cycloalkyl, (C1-C10) alkoxy, (C3-C10)cycloalkoxy, (C3-C10)cycloalkyl(C1-C10)alkyl, (C3-C10)cycloalkoxy(C1-C10)alkyl, (C3-C10) cycloalkyl(C1-C10)alkoxy, (C3-C10)cycloalkoxy(C1-C10) alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring;
such that selective hydrolysis of a phosphite ester group of the monodentate ligand of formula (IV) in the ligand blend with respect to hydrolysis of a phosphite ester group of the bidentate ligand of formula (III) or the tridentate ligand of formula (IIIA) in the ligand blend occurs, to provide a hydrolysis product; and,
ii) separating the hydrolysis catalyst and the hydrolysis product from the ligand blend by liquid-liquid extraction, such that a concentration of the bidentate ligand is maintained within the concentration range.

Again, for the sake of brevity, the examples are not specifically recapitulated in the description below, but it is apparent that analogous examples are disclosed and claimed herein, corresponding to those described above.

In carrying out the inventive process of maintaining ligand concentrations within a range, i.e., maintaining favored ligand proportions as dictated by the optimized reaction parameters for the reaction, e.g., the hydrocyanation reaction, the hydrolysis catalyst of formula (I) can a hydrolysis product of at least one of the phosphorus-containing ligand of formula (III), (IIIA), or (IV), produced in a reaction milieu of hydrocyanation of an olefin, or is added to the reaction milieu, or both. In particular, the hydrolysis catalyst of formula (I) can be a hydrolysis product of the monodentate ligand of formula (IV). The concentrations of the various components of the ligand blend can be monitored throughout the hydrocyanation process, and in a continuous hydrocyanation process, the relative concentrations of ligands for the metal-ligand catalyst (e.g., a nickel-phosphorus-based ligand complex) are continuously monitored. These relative ligand proportions can be adjusted through selective hydrolysis and removal (e.g., by extraction) of ligand blend components that become excessive in proportion to other ligand blend components.

As described above, and further described in the examples below, the removal step ii) can be through extraction between a nonpolar and a polar organic solvent. Unwanted components can be removed up to the point that a favored concentration is achieved for each of the ligand blend components. Again, the nonpolar solvent can comprise cyclohexane, and the polar solvent can be the raffinate from extraction of the reaction milieu resulting from the hydrocyanation reaction of butadiene, so can comprise pentenenitriles, can comprise adiponitrile, or both.

Again, the components of the ligand blend of formulas (III), (IIIA), and/or (IV) can be any of those described above, as can be the hydrolysis catalyst of formula (I).

The ligand blend can include multiple ligands, such as a mixture of:

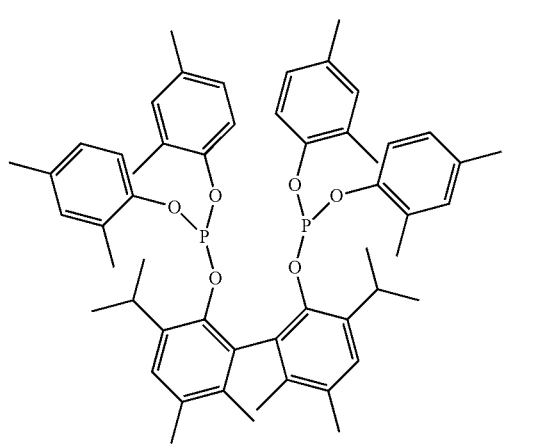

(V)

and monodentate ligands of formula (IV), including the monodentate ligand of formula (XIII)

(XIII)

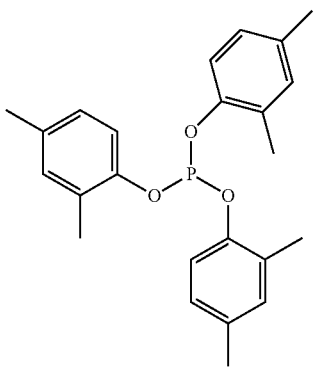

and the monodentate ligand of formula (XIV):

(XIV)

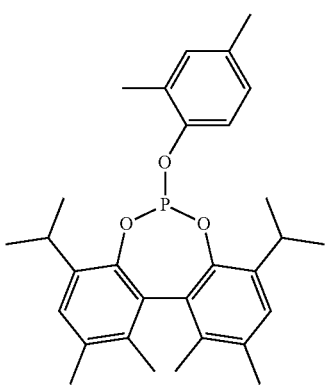

or is a mixture thereof;
wherein the hydrolysis catalyst is of the formula (IA2):

(IA2)

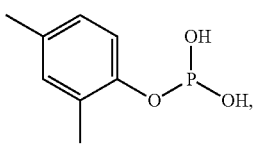

or is of formula (IB2):

(IB2)

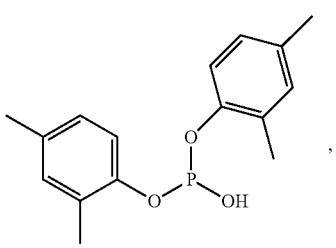

or is a mixture thereof.

By use of the inventive process, the relative proportions of these ligands can controlled through monitoring, addition of hydrolysis catalyst if needed, and removal of acidic hydrolysis products resulting from selective hydrolysis of (one or more) monodentate ligands in the presence of the (one or more) bidentate (or tridentate) ligands. The reaction milieu can further comprise cyclohexane and/or toluene, and one or more nitriles such as 3-pentenenitrile and/or adiponitrile.

EXAMPLES

Materials

Diphosphite bidentate ligand (V) can be prepared according to the procedure published in International Application Number PCT/US 10/60381, International Application Number PCT/US 10/60388, International Application Number PCT/US 11/40193. A solution of ligand (V) was a mixture in toluene with the major component (exclusive of solvent) being (V), but also including (XIII), (XIV), and hydrolysis products of (V), (XIII), or (XIV), and other products derived from the compounds used for (V) synthesis. A portion of the toluene was distilled and (V) ligand mixture subsequently dissolved in cyclohexane. An example composition of the (V) ligand solution in cyclohexane by $^{31}$P NMR is given in Table 1 as example 1 and by HPLC analysis in Table 2.

Example 1: Ligand (V) Solution in Cyclohexane was Subsequently Exposed to Water and Heat The experiment was conducted in a 10 ml glass serum vial with a rectangular stir bar and sealed with a Teflon coated septa using a temperature-regulated Reacti-Block™ aluminum heating block enclosed in a nitrogen purge box and heated to 65° C. The serum vial was charged with a solution of ligand in cyclohexane, inside a glove-box. Water was added by microsyringe to an initial concentration 2000 or 5000 ppm$_w$. Samples were removed at desired intervals for analysis by HPLC and $^{31}$P NMR for (V), (XIII), (VIV), 2,4-xylenol and ligand hydrolysis product of (V) (LHP-V) product concentration. Results are provided below in Table 1, referring to ligands of formulas (V) (bidentate) and (XIII) and (XIV) (monodentate), and in Table 2, providing water hydrolysis rates of ligand (V), see below.

TABLE 1

$^{31}$P NMR analysis of ligand mixture before and after adiponitrile washes.

| Example | (XIII) | (XIV) | (V) | Acidic Phosphorous compounds | Other triaryl phosphites |
|---|---|---|---|---|---|
| (V) Solution (example 1) | 11.0 | 4.3 | 72.1 | 3.2 | 9.2 |
| (V) Solution after 2 washes with Adiponitrile (example 2) | 10.7 | 4.5 | 73.7 | 1.3 | 9.6 |
| Lower Layer 1 (example 4) | 23.5 | 4.2 | 4.1 | 63.8 | 4.4 |
| Lower Layer 2 (example 4) | 11.1 | 4.4 | 21.4 | 35.0 | 8.5 |
| Top layer after 2 washes of Adiponitrile (Example 4) | 11.1 | 4.4 | 73.8 | 1.6 | 8.8 |

*Molar Percentage of phosphorus atoms in each compound.

TABLE 2

Water hydrolysis rate of (V) with and without contacting the ligand solution with adiponitrile.

| Example | Time | Initial water concentration ($ppm_w$) | V (% wt) | LHP-V (% wt) | 2,4-xylenol (% wt) | 7 (% wt) | 8 (% wt) | water, $ppm_w$ (consumption based on Δ2,4-xylenol) |
|---|---|---|---|---|---|---|---|---|
| V solution | | | 34.9% | 0.5% | 0.4% | 4.4% | 2.4% | |
| 1 | 0 h | 2000 $ppm_w$ | 34.8% | 0.5% | 0.4% | 4.4% | 2.5% | |
| 1 | 6 h | 2000 $ppm_w$ | 31.7% | 2.5% | 1.2% | 3.7% | 2.5% | 1270 |
| 2 | 0 h | 2000 $ppm_w$ | 36.4% | 0.6% | 0.1% | 4.4% | 2.6% | |
| 2 | 6 h | 2000 $ppm_w$ | 37.3% | 0.9% | 0.2% | 4.4% | 2.6% | 170 |
| 1 | 0 h | 5000 $ppm_w$ | 34.8% | 0.5% | 0.4% | 4.4% | 2.5% | |
| 1 | 4 h | 5000 $ppm_w$ | 29.8% | 3.5% | 1.5% | 3.4% | 2.4% | 1620 |
| 2 | 0 h | 5000 $ppm_w$ | 36.4% | 0.6% | 0.1% | 4.4% | 2.6% | |
| 2 | 4 h | 5000 $ppm_w$ | 36.6% | 0.6% | 0.1% | 4.4% | 2.6% | 50 |

Example 2: (V) Ligand Mixture in Cyclohexane was Contacted with Adiponitrile and Subsequently Exposed to Water and Heat In a separatory funnel, ligand (20 g) was mixed with 5 g of adiponitrile. The lower layer was removed and additional 5 g of adiponitrile was added. The lower layer was again removed and the resulting upper layer was analyzed by HPLC and $^{31}$P NMR for changes. The acidic ligand hydrolysis products were reduced from 3.2 to 1.3 mol % of the phosphorus content by $^{31}$P NMR analysis, Table 1.

A 10 ml glass serum vial was charged with 5 g of the upper layer solution and water was added by microsyringe to an initial concentration 2000 or 5000 $ppm_w$. The experiment with water was conducted in a 10 ml glass serum vial with a rectangular stir bar and sealed with a Teflon coated septa using a temperature-regulated Reacti-Block™ aluminum heating block heated to 65° C. The heating block was enclosed in a nitrogen purge box. Samples were removed at desired intervals for analysis by HPLC for V, 7, 8, 2,4-xylenol and LHP-V product concentration.

Pentenenitrile Solution Reactivity with Ligand

Example 3: Addition of Phosphorous Acid

Phosphorous acid ($PO_3H_3$) was added to ligand (V) solution in cyclohexane to obtain 800 $ppm_w$ $PO_3H_3$ in solution. A 10 ml glass serum vial was charged with 1.3 g of 800 ppm, $PO_3H_3$ ligand (V) solution in cyclohexane, 3.7 g of mixture of pentenenitrile isomers, and water added to a concentration of the water for the total mixture to be 2000 $ppm_w$. The experiment with water was conducted in a 10 ml glass serum vial with a rectangular stir bar and sealed with a Teflon coated septa using a temperature-regulated Reacti-Block™ aluminum heating block heated to 65° C. The heating block was enclosed in a nitrogen purge box. Samples were removed at desired intervals for analysis by HPLC for (V), (XIII), (XIV), 2,4-xylenol and LHP-V product concentration.

Example 4: Removal of Acidic Phosphorous Ester Groups by Contacting with Adiponitrile Phosphorous acid ($PO_3H_3$) was added to ligand solution (V) in cyclohexane to obtain 800 $ppm_w$ $PO_3H_3$ in solution. In a separatory funnel, 20 g of the 800 $ppm_w$ $PO_3H_3$ ligand (V) solution in cyclohexane was mixed with 5 g of adiponitrile. The lower layer was removed and additional 5 g of adiponitrile was added. The lower layer was again removed and the resulting upper layer was analyzed by HPLC and $^{31}$P NMR for changes. The extraction results in removing many acidic ligand hydrolysis products in the lower layer as shown in the phosphorus analysis by $^{31}$P NMR in table 1. A 10 ml glass serum vial was charged with 1.3 g of the upper layer, and 3.7 g of a mixture of pentenenitriles isomers, and water to obtain an initial concentration 2000 $ppm_w$. inside a glove-box. The experiment with water was conducted in a 10 ml glass serum vial with a rectangular stir bar and sealed with a Teflon coated septa using a temperature-regulated Reacti-Block™ aluminum heating block heated to 65° C. and enclosed in a nitrogen purge box. Samples were removed at desired intervals for analysis by HPLC for (V), (XIII), (XIV), 2,4-xylenol and LHP-V product concentration.

Pentenenitrile Solution Reactivity with Ligand at 75° C.

Example 5: Addition of Phosphorous Acid

Phosphorous acid ($PO_3H_3$) was added to ligand (V) solution in cyclohexane to obtain 400 $ppm_w$ $PO_3H_3$ in solution. A 10 ml glass serum vial was charged with 1.3 g of the 400 $ppm_w$ $PO_3H_3$ ligand (V) solution in cyclohexane, 3.8 g of mixture of pentenenitrile isomers, and water added to an initial concentration of the water for the total mixture to be 6000 $ppm_w$. The experiment with water was conducted in a 10 ml glass serum vial with a rectangular stir bar and sealed with a Teflon coated septa using a temperature-regulated Reacti-Block™ aluminum heating block heated to 75° C. The heating block was enclosed in a nitrogen purge box. Samples were removed at desired intervals for analysis by HPLC for (V), (XIII), (XIV), 2,4-xylenol and one hydrolysis product of formula V (LHP-V) concentration.

Example 6: Removal of Acidic Phosphorous Ester Groups by Contacting the Ligand (V) Solution with Adiponitrile Phosphorous acid ($H_3PO_3$) was added to ligand solution in cyclohexane to obtain 400 $ppm_w$ $PO_3H_3$ in solution. In a separatory funnel, 20 g of the 400 $ppm_w$ $PO_3H_3$ ligand (V) solution in cyclohexane was mixed with 5 g of adiponitrile. The lower layer was removed and additional 5 g of adiponitrile was added. The lower layer was again removed. A 10 ml glass serum vial was charged with a 1.3 g of the upper layer and 3.7 g of a mixture of pentenenitriles isomers. Water was added by microsyringe to an initial concentration 6000 ppm$_w$. The experiment with water was conducted in a 10 ml glass serum vial with a rectangular stir bar and sealed with a Teflon coated septa using a temperature-regulated Reacti-Block™ aluminum heating block heated to 75° C. The heating block was enclosed in a nitrogen purge box. Samples were removed at desired intervals for analysis by HPLC for (V), (XIII), (XIV), 2,4-xylenol and LHP-V product concentration. Results are provided in Table 3, below.

TABLE 3

Results of Example 6

| Example | Time | Initial water concentration (ppm$_w$) | V (% wt) | LHP-V (% wt) | 2,4-xylenol (% wt) | 7 (% wt) | 8 (% wt) | water, ppm$_w$ (consumption based on Δ2,4-xylenol) |
|---|---|---|---|---|---|---|---|---|
| 3 | 0 h | 2000 ppm$_w$ | 9.0% | 0.2% | 0.1% | 1.2% | 0.6% | |
| 3 | 6 h | 2000 ppm$_w$ | 9.1% | 0.3% | 0.1% | 1.2% | 0.6% | 40 |
| 3 | 24 h | 2000 ppm$_w$ | 5.5% | 1.9% | 1.0% | 0.6% | 0.6% | 1300 |
| 4 | 0 h | 2000 ppm$_w$ | 9.1% | 0.2% | 0.0% | 1.1% | 0.6% | |
| 4 | 6 h | 2000 ppm$_w$ | 9.2% | 0.2% | 0.0% | 1.1% | 0.7% | <10 |
| 4 | 24 h | 2000 ppm$_w$ | 9.0% | 0.3% | 0.1% | 1.1% | 0.7% | 50 |
| 5 | 0 h | 6000 ppm$_w$ | 8.8% | 0.2% | 0.1% | 1.1% | 0.6% | |
| 5 | 6 h | 6000 ppm$_w$ | 4.3% | 2.2% | 1.2% | 0.4% | 0.5% | 1590 |
| 6 | 0 h | 6000 ppm$_w$ | 9.4% | 0.2% | 0.0% | 1.1% | 0.6% | |
| 6 | 6 h | 6000 ppm$_w$ | 9.4% | 0.3% | 0.0% | 1.1% | 0.6% | <30 |

Statements of the Invention:

Various statements of the present invention are described below.

1. A process of hydrolyzing a phosphorus-based ligand for a transition metal catalyst, wherein the ligand comprises at least one phosphite ester group; the process comprising:
i) contacting a hydrolysis catalyst of formula (I)

$$(R^{11}X^{11})_nP(OH)_{3-n} \quad (I)$$

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl(C1-C10)alkyl, (C6-C20)aryl, or (C6-C20)aryl(C1-C10) alkyl, wherein for any (C6-C20)aryl or (C6-C20)aryl(C1-C10)alkyl of $R^{11}$, each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring;
with one or more phosphorus-based ligand selected from the group consisting of:
a bidentate phosphorus-based ligand of formula (III)

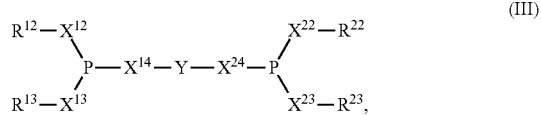

(III)

a tridentate phosphorus-based ligand of formula (IIIA)

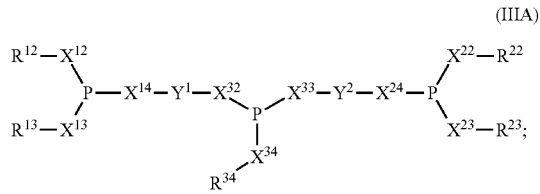

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;
and
a monodentate phosphorus-based ligand of formula (IV)

$$P(X^1R^1)(X^2R^2)(X^3R^3) \quad (IV)$$

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^1$, $R^2$, or $R^3$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring; and a mixture thereof;

in the presence of water and, optionally, one or more organic liquids, under conditions of time, temperature, and concentration sufficient to bring about hydrolysis of the at least one phosphite ester bond to provide a hydrolysis product; and ii) separating the hydrolysis catalyst and the hydrolysis product from the ligand by liquid-liquid extraction.

2. The process of statement 1, wherein $R^1$, $R^2$, $R^3$, $R^{11}$, $R^{12}$, $R^{13}$, $R^{22}$, $R^{23}$ or $R^{34}$ is each an independently selected (C6-C20)aryl group, which is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, or wherein one or more pair of $R^1$ and $R^2$, or $R^{12}$ and $R^{13}$, or $R^{22}$ and $R^{23}$, or when n=2, two $R^{11}$, is directly mutually bonded such that any pair together with the respective $X^1$, $X^2$, $X^{11}$, $X^{12}$, $X^{13}$, $X^{22}$ or $X^{23}$ groups and the phosphorus atom to which they are bonded, forms a ring.

3. The process of any one of statements 1-2, wherein each independently selected $R^1$, $R^2$, $R^3$, $R^{11}$, $R^{12}$, $R^{13}$, $R^{22}$, $R^{23}$ or $R^{34}$ is a group of formula (II)

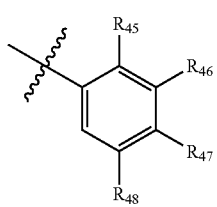

(II)

wherein a wavy line indicates a point of attachment; and wherein $R^{45}$ is selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

4. The process of any one of statements 1-3, wherein Y, or independently selected $Y^1$ or $Y^2$, is a (C6-C20)arylene group, wherein each ring thereof is independently unsubstituted or is substituted independently with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

5. The process of any one of statements 1-4, wherein the hydrolysis catalyst of formula (I) is a hydrolysis product of at least one of the phosphorus-containing ligand of formula (III), (IIIA), or (IV), produced in a reaction milieu of hydrocyanation of an olefin, or is added to the reaction milieu, or both.

6. The process of any one of statements 1-5, wherein the removal step ii) is through extraction between a nonpolar and a polar organic solvent.

7. The process of statement 6, wherein the nonpolar solvent comprises cyclohexane.

8. The process of statement 6, wherein the polar solvent is a raffinate from the hydrocyanation reaction of butadiene, comprises adiponitrile, or both.

9. The process of any one of statements 1-8, comprising the ligand of formula (III) is of formula (X):

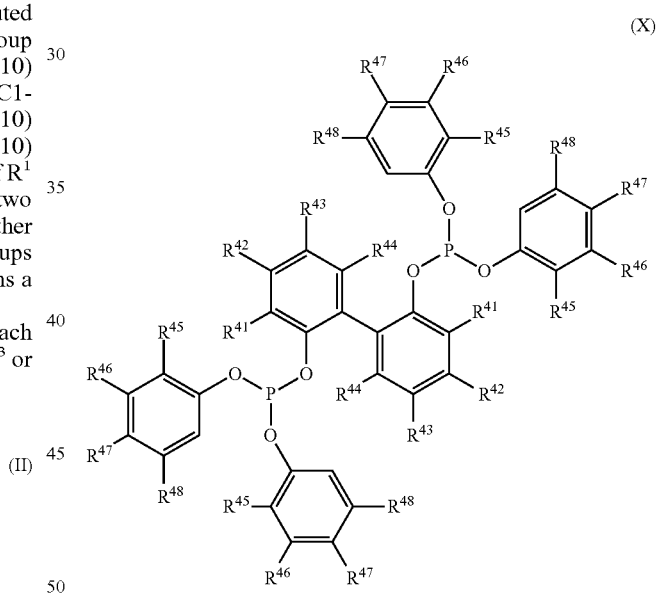

(X)

wherein each $R^{41}$ and $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

10. The process of statement 9, wherein for the ligand of formula (X), $R^{41}$ is methyl, ethyl, isopropyl or cyclopentyl;

$R^{42}$ is H or methyl;

$R^{43}$ is H or (C1-C4)alkyl;
$R^{44}$ is H or methyl;
$R^{45}$ is methyl, ethyl, or isopropyl; and
$R^{46}$, $R^{47}$ and $R^{48}$ are independently H or (C1-C4)alkyl.

11. The process of any one of statements 1-8, wherein the ligand of formula (III) is of formula (VII):

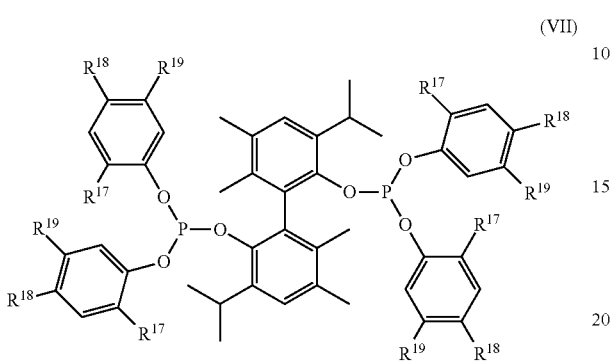

(VII)

wherein $R^{17}$ is methyl, ethyl or iso-propyl, and $R^{18}$ and $R^{19}$ are independently H or methyl.

12. The process of any one of statements 1-8, wherein the ligand of formula (III) is of formula (XII)

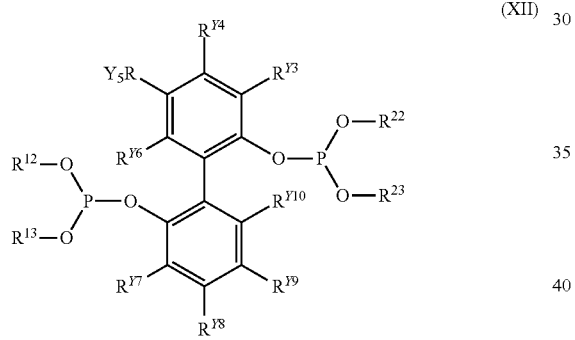

(XII)

wherein $R^{12}$, $R^{13}$, $R^{22}$ and $R^{23}$ are each independently an unsubstituted or a substituted monovalent aryl, and each of $R^{Y3}$—$R^{Y10}$ is independently selected from the group consisting of hydrogen, (C1-C10) alkyl, and (C1-C10)alkoxy, or wherein two adjacent $R^{Y3}$—$R^{Y10}$ groups together form an optionally substituted fused aryl ring.

13. The process of statement 12, wherein $R^{12}$, $R^{13}$, $R^{22}$, and $R^{23}$ are each independently phenyl substituted at a respective first ortho-position with a (C1-C10)alkyl or (C1-C10) alkoxy, at a respective second ortho-position with hydrogen, and wherein respective meta- and para-positions of the $R^{12}$, $R^{13}$, $R^{22}$, and $R^{23}$ phenyls can each independently be unsubstituted or be substituted independently with 1-3 (C1-C10) alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

14. The process of any one of statements 1-8, wherein the ligand of formula (III) is of formula (V):

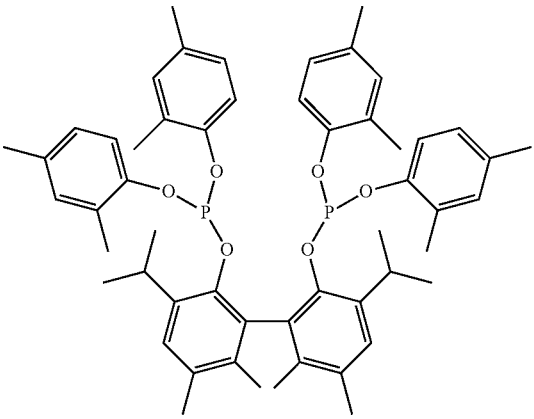

(V)

15. The process of any one of statements 1-14, wherein the hydrolysis catalyst is of formula (IA1):

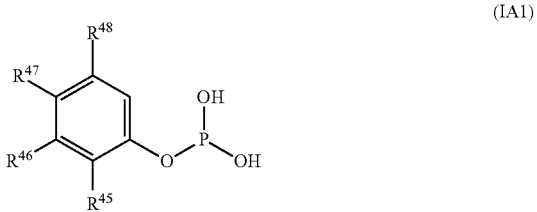

(IA1)

or is of formula (IB1):

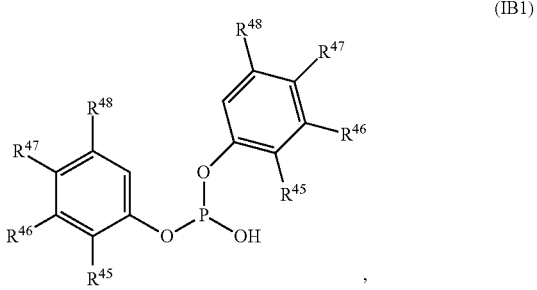

(IB1)

or is a mixture thereof;

wherein $R^{45}$ is selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

16. The process of statement 15, wherein for the hydrolysis catalyst of formula (IA1) or (IB1) or both, $R^{45}$ is methyl, ethyl or isopropyl.

17. The process of statement 15, wherein in the hydrolysis catalyst of formula (IA1) of (IB1) or both, $R^{45}$ is methyl, ethyl or isopropyl, $R^{46}$ is hydrogen, and $R^{47}$ and $R^{48}$ are independently hydrogen or methyl.

18. The process of any one of statements 1-17 wherein the hydrolysis catalyst is of formula (IA2):

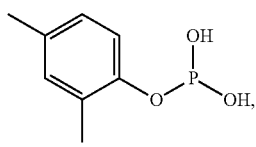

(IA2)

or is of formula (IB2):

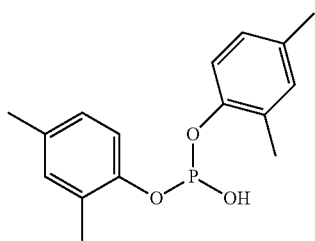

(IB2)

or a mixture thereof.

19. A process for modifying the relative ratio of two phosphorus-based ligands for a transition metal catalyst, wherein each ligand in the blend comprises at least one phosphite ester group, in a ligand blend comprising at least two phosphorus-based ligands, a first component of the blend being selected from the group consisting of a bidentate phosphorus-based ligand of formula (III) and a tridentate phosphorus-based ligand of formula (IIIA):

a bidentate phosphorus-based ligand of formula (III)

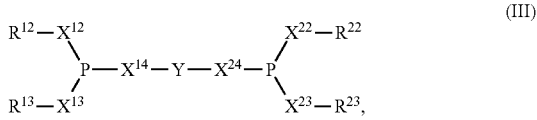

(III)

a tridentate phosphorus-based ligand of formula (IIA)

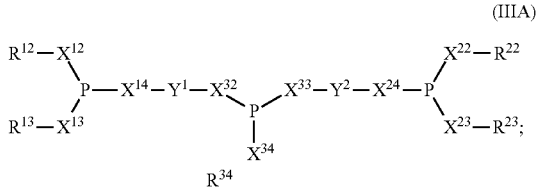

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10) alkyl, (C3-C10)cycloalkyl(C1-C10)alkoxy, (C3-C10)cycloalkoxy(C1-C10)alkoxy, (C6-C20)aryl, and (C6-C20)aryl (C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted independently with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10) alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10) haloalkyl;

and, a second component of the blend being a ligand comprising a monodentate phosphorus-based ligand of formula (IV)

$$P(X^1R^1)(X^2R^2)(X^3R^3) \qquad (IV)$$

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10) alkyl, (C3-C10)cycloalkyl, (C3-C10)cycloalkyl(C1-C10) alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$, each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

the process comprising:

i) selectively hydrolyzing a phosphite ester group of the second component of the ligand blend with respect to a phosphite ester group of the first component of the ligand blend, by contacting the blend with a hydrolysis catalyst of formula (I)

$$(R^{11}X^{11})_nP(OH)_{3-n} \qquad (I)$$

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl (C1-C10)alkyl, (C6-C20)aryl, or (C6-C20)aryl(C1-C10) alkyl, wherein for any (C6-C20)aryl or (C6-C20)aryl(C1-C10)alkyl of $R^{11}$, each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring;

in the presence of water and, optionally, one or more organic liquids, under conditions of time, temperature, and concentration sufficient to bring about hydrolysis of the at least one phosphite ester bond of the second component to provide a hydrolysis product, and ii) separating the hydrolysis catalyst and the hydrolysis product from the ligand blend by liquid-liquid extraction.

20. The process of statement 19, wherein $R^1$, $R^2$, $R^3$, $R^{11}$, $R^{12}$, $R^{13}$, $R^{22}$, $R^{23}$ or $R^{34}$ is each an independently selected (C6-C20)aryl group, which is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, or wherein one or more pair of $R^1$ and $R^2$, or $R^{12}$ and $R^{13}$, or $R^{22}$ and $R^{23}$, or when n=2, two $R^{11}$, is directly mutually bonded such that any pair together with the respective $X^1$, $X^2$, $X^{11}$, $X^{12}$, $X^{13}$, $X^{22}$ or $X^{23}$ groups and the phosphorus atom to which they are bonded, forms a ring.

21. The process of any one of statements 19-20, wherein each independently selected $R^1$, $R^2$, $R^3$, $R^{11}$, $R^{12}$, $R^{13}$, $R^{22}$, $R^{23}$ or $R^{34}$ is a group of formula (II)

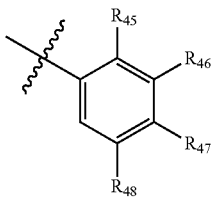

(II)

wherein a wavy line indicates a point of attachment; and wherein $R^{45}$ is selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

22. The process of any one of statements 19-21 wherein Y, or independently selected $Y^1$ or $Y^2$, is a (C6-C20)arylene group, wherein each ring thereof is independently unsubstituted or is substituted independently with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

23. The process of any one of statements 19-22, wherein the hydrolysis catalyst of formula (I) is a hydrolysis product of at least one of the phosphorus-containing ligand of formula (III), (IIIA), or (IV), produced in a reaction milieu of hydrocyanation of an olefin, or is added to the reaction milieu, or both.

24. The process of any one of statements 19-23, wherein the removal step ii) is through extraction between a nonpolar and a polar organic solvent.

25. The process of statement 24, wherein the nonpolar solvent comprises cyclohexane.

26. The process of any one of statements 24-25, wherein the polar solvent is a raffinate from the hydrocyanation reaction of butadiene, comprises adiponitrile, or both.

27. The process of any one of statements 19-26, comprising the ligand of formula (III) is of formula (X):

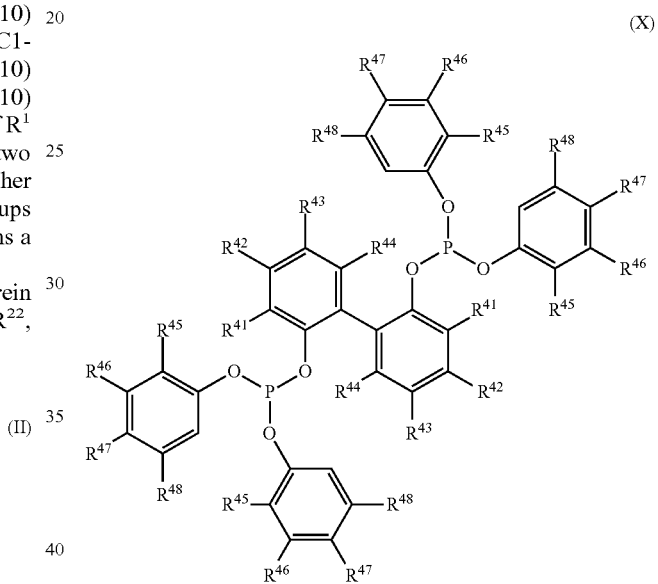

(X)

wherein each $R^{41}$ and $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

28. The process of statement 27, wherein for the ligand of formula (X), $R^{41}$ is methyl, ethyl, isopropyl, or cyclopentyl;

$R^{42}$ is H or methyl;

$R^{43}$ is H or (C1-C4)alkyl;

$R^{44}$ is H or methyl;

$R^{45}$ is methyl, ethyl, or isopropyl; and $R^{46}$, $R^{47}$ and $R^{48}$ are independently H or (C1-C4)alkyl.

29. The process of any one of statements 19-26, wherein the ligand of formula (III) is of formula (VII):

(VII)

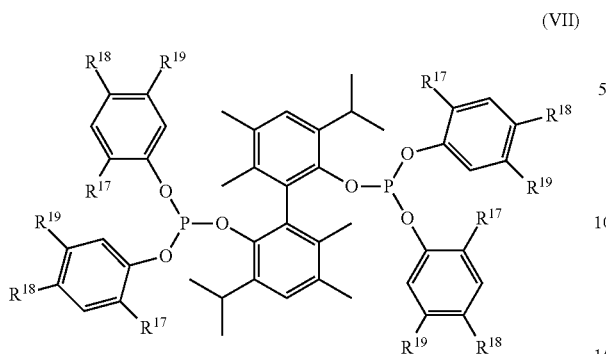

wherein $R^{17}$ is methyl, ethyl or iso-propyl, and $R^{18}$ and $R^{19}$ are independently H or methyl.

30. The process of any one of statements 19-26, wherein the ligand of formula (III) is of (XII)

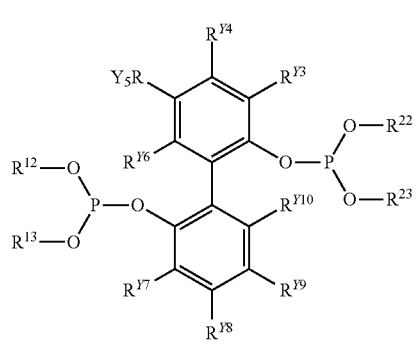

wherein $R^{12}$, $R^{13}$, $R^{22}$ and $R^{23}$ are each independently an unsubstituted or a substituted monovalent aryl, and each of $R^{Y3}$—$R^{Y10}$ is independently selected from the group consisting of hydrogen, (C1-C10) alkyl, and (C1-C10)alkoxy, or wherein two adjacent $R^{Y3}$—$R^{Y10}$ groups together form an optionally substituted fused aryl ring.

31. The process of statement 30, wherein $R^{12}$, $R^{13}$, $R^{22}$, and $R^{23}$ are each independently phenyl substituted at a respective first ortho-position with a (C1-C10)alkyl or (C1-C10)alkoxy, at a respective second ortho-position with hydrogen, and wherein respective meta- and para-positions of the $R^{12}$, $R^{13}$, $R^{22}$, and $R^{23}$ phenyls can each independently be unsubstituted or be independently substituted with 1-3 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

32. The process of any one of statements 19-26, wherein the ligand of formula (III) is of formula (V):

(V)

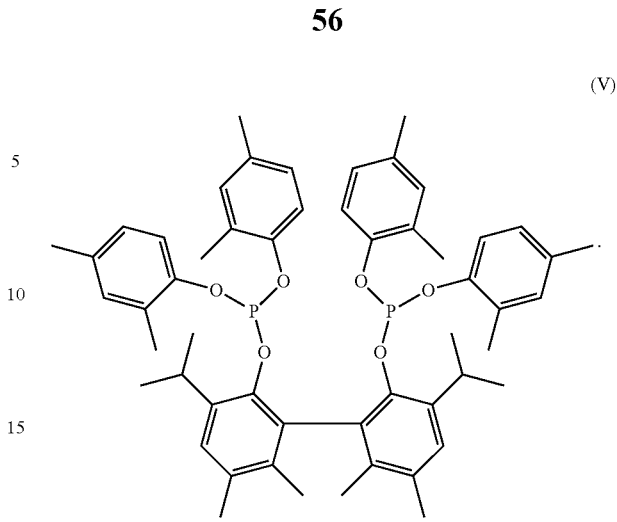

33. The process of any one of statements 19-32 wherein the hydrolysis catalyst is of formula (IA1):

(IA1)

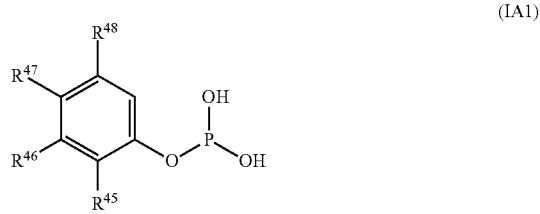

or is of formula (IB1):

(IB1)

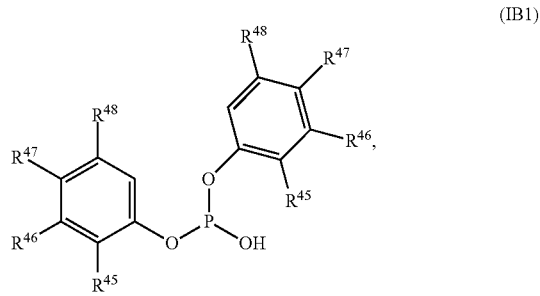

or a mixture thereof;

wherein each $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

34. The process of statement 33, wherein for the hydrolysis catalyst of formula (IA1), (IB1), or both, $R^{45}$ is methyl, ethyl, or isopropyl.

35. The process of statement 33, wherein for the hydrolysis catalyst of formula (IA1), (IB1), or both, $R^{45}$ is methyl, ethyl or isopropyl, $R^{46}$ is hydrogen, and $R^{47}$ and $R^{48}$ are independently hydrogen or methyl.

36. The process of any one of statements 19-35 wherein the hydrolysis catalyst is of formula (IA2):

(IA2)

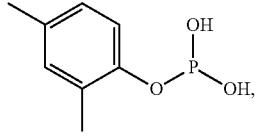

or is of formula (IB2):

(IB2)

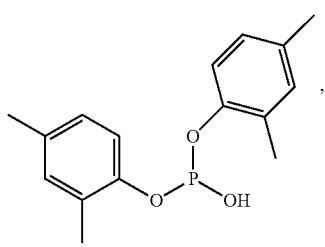

or is a mixture thereof.

37. The method of statement 19, wherein the bidentate ligand of formula (III) is formula (V), (V)

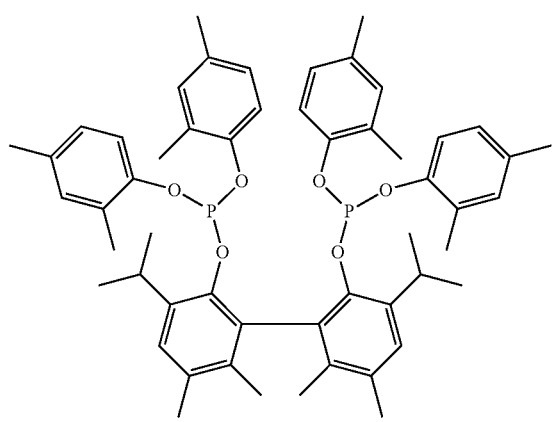

and the monodentate ligand is of formula (XIII)

(XIII)

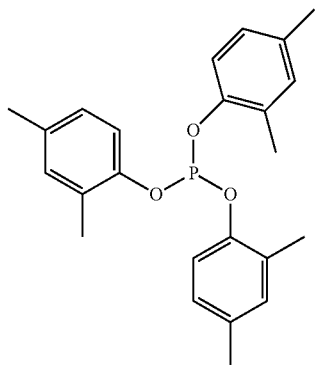

or is of formula (XIV):

(XIV)

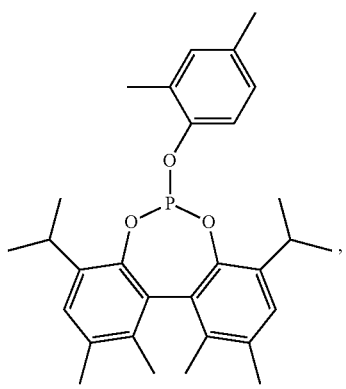

or is a mixture thereof;
and the hydrolysis catalyst is of the formula (IA2):

(IA2)

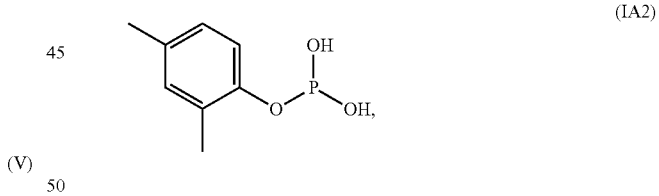

or is of formula (IB2):

(IB2)

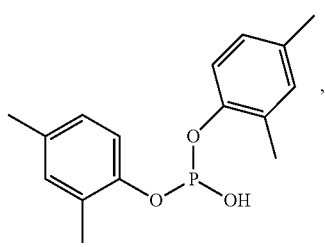

or is a mixture thereof.

38. The process of statement 23, wherein the reaction milieu further comprises cyclohexane and/or toluene.

39. The process of any one of statements 23-38, wherein the reaction milieu further comprises one or more nitriles.

40. The process of statement 39, wherein the nitriles comprise 3-pentenenitrile.

41. The process of any one of statements 39-40, wherein the nitriles comprise adiponitrile.

42. A process for maintaining a concentration of a phosphorus-based bidentate ligand or of a phosphorus-based tridentate ligand, or both, within a concentration range, in a phosphorus-based ligand blend further comprising a monodentate phosphorus-based ligand, for a transition metal catalytic complex in a hydrocyanation reaction milieu comprising water and at least one organic liquid, wherein each phosphorus-based ligand in the blend comprises at least one phosphite ester group, the ligand blend comprising at least two phosphorus-based ligands, a first component of the ligand blend being a bidentate phosphorus-based ligand of formula (III) or a tridentate phosphorus-based ligand of formula (IIIA), or a mixture thereof:

a bidentate phosphorus-based ligand of formula (III)

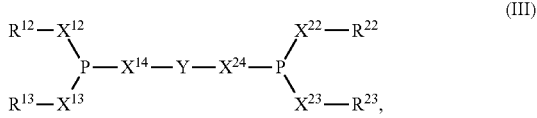

(III)

a tridentate phosphorus-based ligand of formula (IIIA)

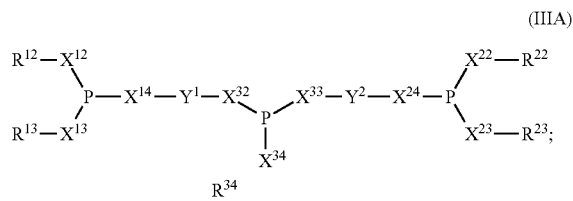

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl; and, a second component of the blend being a monodentate phosphorus-based ligand of formula (IV)

$$P(X^1R^1)(X^2R^2)(X^3R^3) \qquad (IV)$$

wherein $X^1$, $X^2$ and $X^3$ are each independently oxygen or a bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^1$, $R^2$, or $R^3$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

the process comprising:

i) contacting the ligand blend in the hydrocyanation reaction milieu with a hydrolysis catalyst of formula (I)

$$(R^{11}X^{11})_nP(OH)_{3-n} \qquad (I)$$

wherein n is 0, 1, or 2, and each $X^{11}$ is independently oxygen or a bond, and each independently selected $R^{11}$ is (C1-C10)alkyl, (C3-C10)cycloalkyl, (C3-C10)cycloalkyl (C1-C10)alkyl, (C6-C20)aryl, or (C6-C20)aryl(C1-C10)alkyl, wherein for any (C6-C20)aryl or (C6-C20)aryl(C1-C10)alkyl of $R^{11}$, each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, when n=2, two $R^{11}$ groups are optionally directly bonded to each other such that the two $R^{11}X^{11}$ groups, together with the phosphorus atom to which they are bonded, form a ring;

such that selective hydrolysis of a phosphite ester group of the monodentate ligand of formula (IV) in the ligand blend with respect to hydrolysis of a phosphite ester group of the bidentate ligand of formula (III) or the tridentate ligand of formula (IIIA), or both, in the ligand blend occurs, to provide a hydrolysis product; and, ii) separating the hydrolysis catalyst and the hydrolysis product from the ligand blend by liquid-liquid extraction, such that a concentration of the bidentate ligand is maintained within the concentration range.

43. The process of statement 42, wherein $R^1$, $R^2$, $R^3$, $R^{11}$, $R^{12}$, $R^{13}$, $R^{22}$, $R^{23}$ or $R^{34}$ is each an independently selected (C6-C20)aryl group, which is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)

alkoxy, and (C6-C20)aryl, or wherein one or more pair of $R^1$ and $R^2$, or $R^{12}$ and $R^{13}$, or $R^{22}$ and $R^{23}$, or when n=2, two $R^{11}$, is directly mutually bonded such that any pair together with the respective $X^1$, $X^2$, $X^{11}$, $X^{12}$, $X^{13}$, $X^{22}$ or $X^{23}$ groups and the phosphorus atom to which they are bonded, forms a ring.

44. The process of any one of statements 42-43, wherein each independently selected $R^1$, $R^2$, $R^3$, $R^{11}$, $R^{12}$, $R^{13}$, $R^{22}$, $R^{23}$ or $R^{34}$ is a group of formula (II)

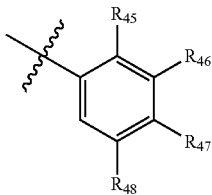
(II)

wherein a wavy line indicates a point of attachment; and wherein $R^{45}$ is selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

45. The process of any one of statements 42-44, wherein Y, or independently selected $Y^1$ or $Y^2$, is a (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

46. The process of any one of statements 42-45, wherein the hydrolysis catalyst of formula (I) is a hydrolysis product of at least one of the phosphorus-containing ligand of formula (III), (IIIA), or (IV), produced in a reaction milieu of hydrocyanation of an olefin, or is added to the reaction milieu, or both.

47. The process of any one of statements 42-46, wherein the removal step ii) is through extraction between a nonpolar and a polar organic solvent.

48. The process of statement 47, wherein the nonpolar solvent comprises cyclohexane.

49. The process of statement 47, wherein the polar solvent is a raffinate from the hydrocyanation reaction of butadiene, comprises adiponitrile, or both.

50. The process of any one of statements 42-49, comprising the ligand of formula (III) is of formula (X):

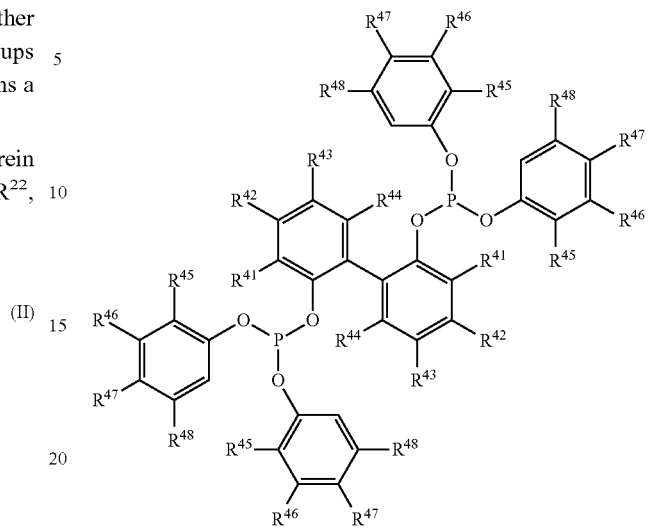
(X)

wherein each $R^{41}$ and $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

51. The process of statement 50, wherein for the ligand of formula (X),
$R^{41}$ is methyl, ethyl, isopropyl, or cyclopentyl;
$R^{42}$ is H or methyl;
$R^{43}$ is H or (C1-C4)alkyl;
$R^{44}$ is H or methyl;
$R^{45}$ is methyl, ethyl, or isopropyl; and
$R^{46}$, $R^{47}$ and $R^{48}$ are independently H or (C1-C4)alkyl.

52. The process of any one of statements 42-49, wherein the ligand of formula (III) is of formula (VII):

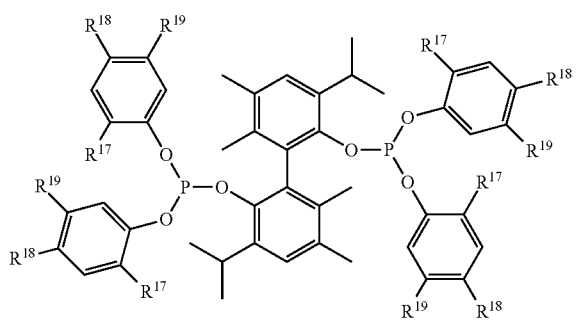
(VII)

wherein $R^{17}$ is methyl, ethyl or iso-propyl, and $R^{11}$ and $R^{19}$ are independently H or methyl.

53. The process of any one of statements 42-49, wherein the ligand of formula (III) is of formula (XII)

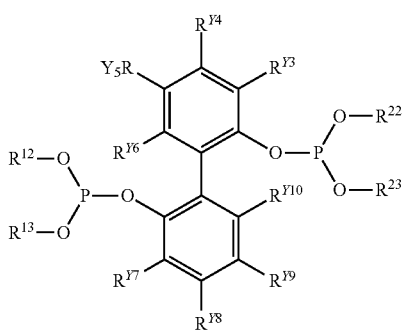

(XII)

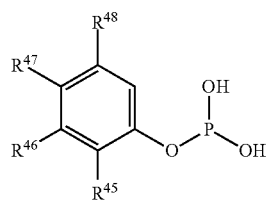

(IA1)

wherein $R^{12}$, $R^{13}$, $R^{22}$ and $R^{23}$ are each independently an unsubstituted or a substituted monovalent aryl, and each of $R^{Y3}$—$R^{Y10}$ is independently selected from the group consisting of hydrogen, (C1-C10) alkyl, and (C1-C10)alkoxy, or wherein two adjacent $R^{Y3}$—$R^{Y10}$ groups together form an optionally substituted fused aryl ring.

54. The process of statement 53, wherein $R^{12}$, $R^{13}$, $R^{22}$, and $R^{23}$ are each independently phenyl substituted at a respective first ortho-position with a (C1-C10)alkyl or (C1-C10)alkoxy, at a respective second ortho-position with hydrogen, and wherein respective meta- and para-positions of the $R^{12}$, $R^{13}$, $R^{22}$, and $R^{23}$ phenyls can each independently be unsubstituted or be independently substituted with 1-3 (C1-C10) alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

55. The process of any one of statements 42-49, wherein the ligand of formula (III) is of formula (V):

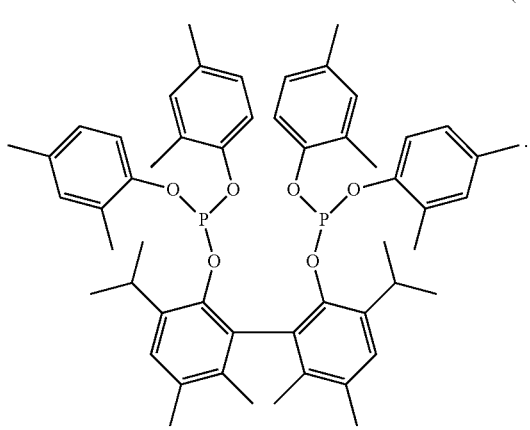

(V)

56. The process of any one of statements 42-55, wherein the hydrolysis catalyst is of formula (IA1):

or is of formula (IB1):

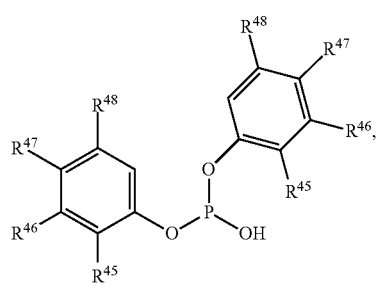

(IB1)

or is a mixture thereof;

wherein $R^{45}$ is selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

57. The process of statement 56, wherein for the hydrolysis catalyst of formula (IA1), (IB1), or both, $R^{45}$ is methyl, ethyl, or isopropyl.

58. The process of statement 56, wherein in the hydrolysis catalyst of formula (IA1), (IB1), or both, $R^{45}$ is methyl, ethyl or isopropyl, $R^{46}$ is hydrogen, and $R^{47}$ and $R^{48}$ are independently H or methyl.

59. The process of any one of statements 42-58 wherein the hydrolysis catalyst is of formula (IA2):

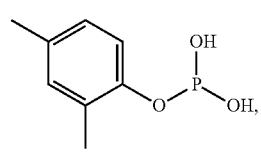

(IA2)

or is of formula (IB2):

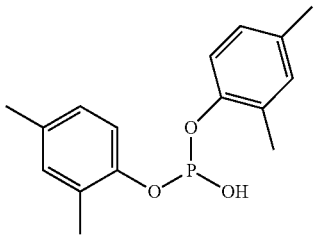

or is a mixture thereof.

60. The method of statement 42, wherein the bidentate ligand is of formula (V),

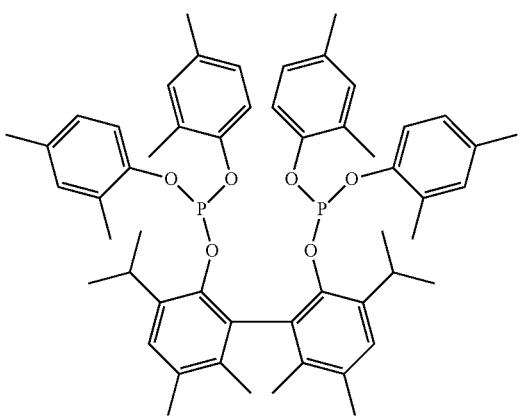

and the monodentate ligand is of formula (XIII)

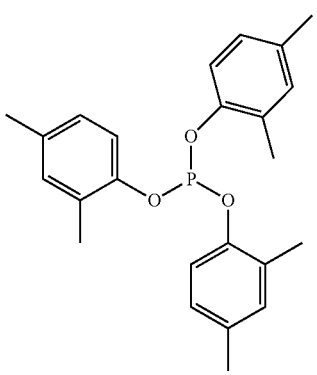

or is of formula (XIV):

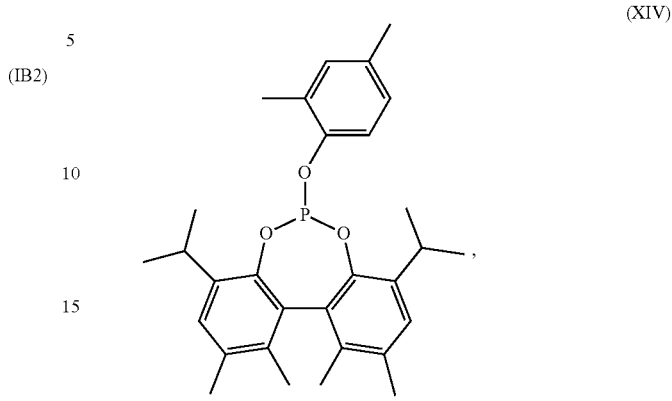

or is a mixture thereof;
and the hydrolysis catalyst is of the formula (IA2):

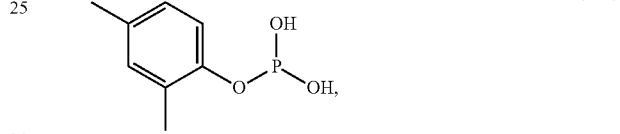

or is of formula (IB2):

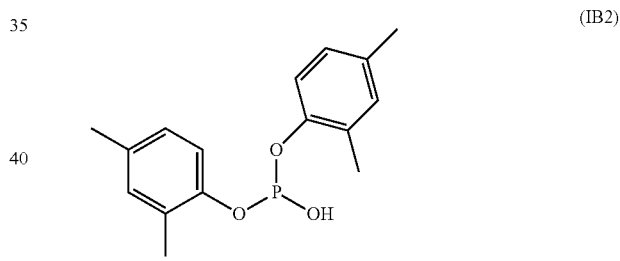

or is a mixture thereof.

61. The process of statement 42, wherein the reaction milieu further comprises cyclohexane and/or toluene.

62. The process of any one of statements 42-61, wherein the reaction milieu further comprises one or more nitriles.

63. The process of statement 62, wherein the nitriles comprise 3-pentenenitrile.

64. The process of any one of statements 62-63, wherein the nitriles comprise adiponitrile.

Accordingly, the foregoing aspects are set forth without any loss of generality to, and without imposing limitations upon any claimed invention. It is to be understood that this disclosure is not limited to particular aspects described, as such can vary. It is also to be understood that the terminology used herein is for the purpose of describing particular aspects only, and is not intended to be limiting, since the scope of the present disclosure will be limited only by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. As will be apparent to those of skill in the art upon reading this disclosure, each of the individual aspects described and illustrated herein has discrete components and features that can be readily separated from or combined with the features of any of the other several examples without departing from the scope or spirit of the present disclosure. Any recited method can be carried out in the order of events recited or in any other order that is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. Applicants reserve the right to physically incorporate into this specification any and all materials and information from any such cited patents or publications. The citation of any publication is for its disclosure prior to the filing date and should not be construed as an admission that the present disclosure is not entitled to antedate such publication by virtue of prior disclosure. Further, the dates of publication provided could be different from the actual publication dates that can need to be independently confirmed. All patents and publications referenced or mentioned herein are also indicative of the levels of skill of those skilled in the art to which the invention pertains.

What is claimed is:

1. A process for maintaining a pre-determined concentration ratio of a monodentate phosphorus ligand and a bidentate phosphorus ligand in a hydrocyanation reaction mixture, comprising:
   i) monitoring the reaction mixture for excess monodentate phosphorus ligand relative to the pre-determined concentration ratio of monodentate phosphorus ligand and bidentate phosphorus ligand;
   ii) contacting the reaction mixture with a hydrolysis catalyst to remove excess monodentate phosphorus ligand by selectively hydrolyzing a phosphite ester group of the monodentate phosphorus ligand in the presence of the bidentate phosphorus ligand to produce a hydrolysis product from the hydrolyzed monodentate phosphorus ligand; and
   iii) separating the hydrolysis catalyst and the hydrolysis product from the reaction mixture by contacting the reaction mixture with a nonpolar solvent and a polar organic solvent to extract the hydrolysis catalyst and the hydrolysis product from the reaction mixture into the polar organic solvent;
wherein
   the hydrolysis catalyst is $H_3PO_3$,

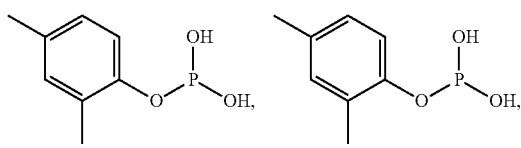

or a mixture thereof;
   the monodentate phosphorus ligand has formula (IV)

(IV)

$X^1$, $X^2$ and $X^3$ are each oxygen and $R^1$, $R^2$ and $R^3$ is each phenyl, each of which is independently unsubstituted or is substituted with 1-4 substituents selected from the group consisting of (C1-C3)alkyl; or, optionally, any two of $R^1$, $R^2$, or $R^3$ are a biphenyl which is unsubstituted or substituted with 1-4 substituents selected from the group consisting of (C1-C3)alkyl, such that any pair of $R^1X^1$, $R^2X^2$, and $R^3X^3$ groups, together with the phosphorus atom to which they are bonded, forms a ring;
the bidentate phosphorus ligand has formula (X)

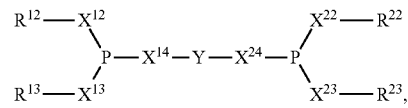

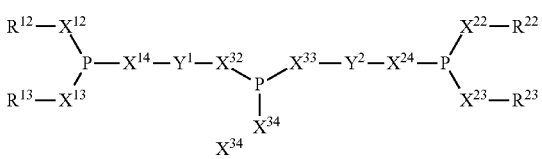

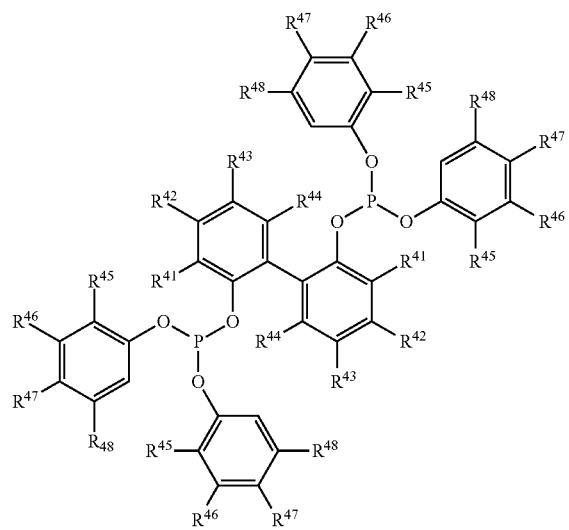

(X)

wherein each of $R^{41}$, $R^{42}$, $R^{43}$, $R^{44}$, $R^{45}$, $R^{46}$, $R^{47}$ and $R^{48}$ is independently H or $(C_1-C_3)$alkyl, or, optionally, any two of $R^{41}$ and $R^{42}$, $R^{42}$ and $R^{43}$, or $R^{43}$ and $R^{44}$ are substituted to form, together, a cyclohexyl ring.

2. The process of claim 1, wherein the hydrolysis catalyst is a hydrolysis product of at least one of the phosphorus-containing ligand of formula (IV) or (X) produced in the reaction mixture, or is added to the reaction mixture, or both.

3. The process of claim 1, wherein the polar organic solvent and the nonpolar solvent form a top layer comprising the nonpolar solvent, the monodentate phosphorus ligand and the bidentate phosphorus ligand, and a bottom layer comprising the polar organic solvent, the hydrolysis catalyst and the hydrolysis product.

4. The process of claim 1, wherein the nonpolar solvent comprises cyclohexane.

5. The process of claim 1, wherein the polar organic solvent is a raffinate from the hydrocyanation reaction of butadiene, comprises adiponitrile, or both.

6. The process of claim 1, wherein for the ligand of formula (X),
$R^{41}$ is methyl, ethyl, or isopropyl;
$R^{42}$ is H or methyl;
$R^{43}$ is H or (C1-C3)alkyl;
$R^{44}$ is H or methyl;
$R^{45}$ is methyl, ethyl, or isopropyl; and
$R^{46}$, $R^{47}$ and $R^{48}$ are independently H or (C1-C3)alkyl.

7. The process of claim 1, wherein the ligand of formula (X) is of formula (VII):

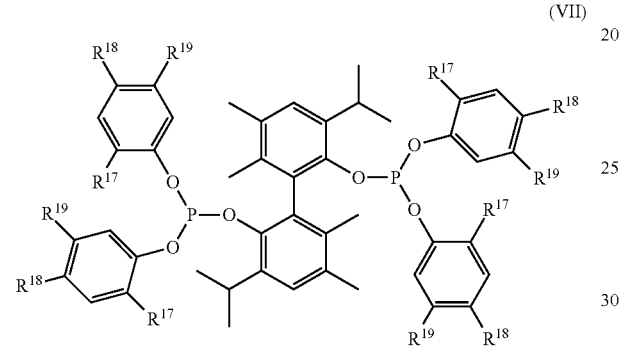

(VII)

wherein $R^{17}$ is methyl, ethyl or iso-propyl, and $R^{18}$ and $R^{19}$ are independently H or methyl.

8. The process of claim 1, wherein the ligand of formula (X) is of formula (XII)

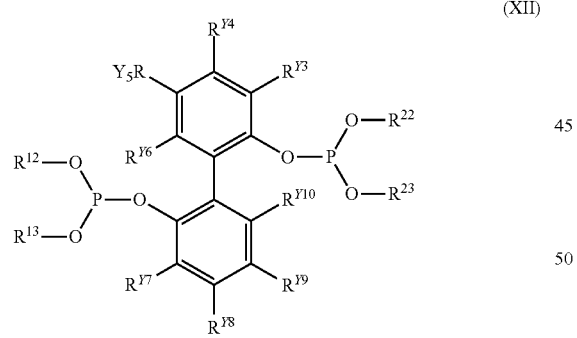

(XII)

wherein $R^{12}$, $R^{13}$, $R^{22}$ and $R^{23}$ are each independently an unsubstituted or a substituted monovalent aryl, and each of $R^{Y3}$—$R^{Y13}$ is independently selected from the group consisting of hydrogen, (C1-C3) alkyl, or wherein two adjacent $R^{Y3}$—$R^{Y10}$ groups together form a cyclohexyl ring.

9. The process of claim 8, wherein $R^{12}$, $R^{13}$, $R^{22}$, and $R^{23}$ are each independently phenyl substituted at a respective first ortho-position with a (C1-C3) alkyl, at a respective second ortho-position with hydrogen, and wherein respective meta- and para-positions of the $R^{12}$, $R^{13}$, $R^{22}$, and $R^{23}$ phenyls can each independently be unsubstituted or be independently substituted with (C1-C3) alkyl;
$R^{Y6}$ and $R^{Y10}$ are independently (C1-C3) alkyl, and $R^{Y3}$, $R^{Y4}$, $R^{Y5}$, $R^{Y7}$, $R^{Y8}$, and $R^{Y9}$, are independently H or (C1-C3) alkyl, provided that at least one of $R^{Y3}$, $R^{Y4}$, or $R^{Y5}$, and at least one of $R^{Y7}$, $R^{Y8}$, or $R^{Y9}$, is (C1-C3) alkyl.

10. The process of claim 1, wherein the ligand of formula (X) is of formula (V):

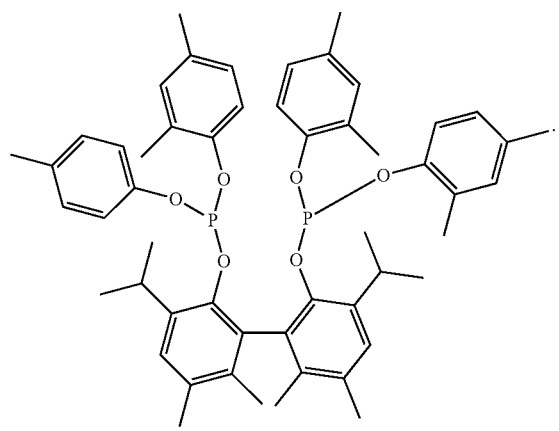

(V)

11. The process of claim 1 wherein the hydrolysis catalyst has the following formula (IA2):

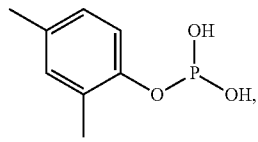

(IA2)

or is of formula (IB2):

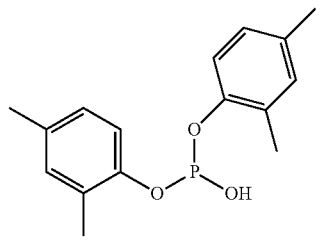

(IB2)

or is a mixture thereof.

12. The method of claim 1, wherein the bidentate phosphorus ligand of formula (X) is formula (V), (V)

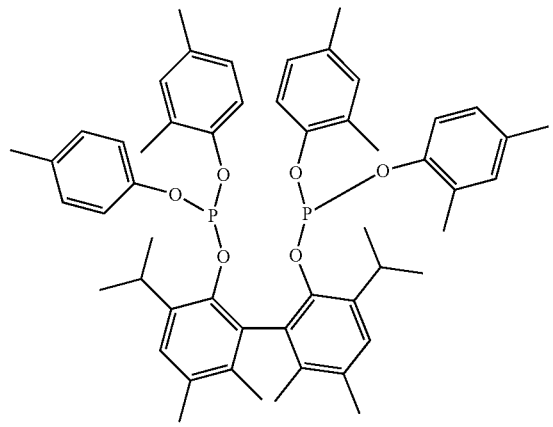

and the monodentate phosphorus ligand of formula (IV) is formula (XIII)

(XIII)

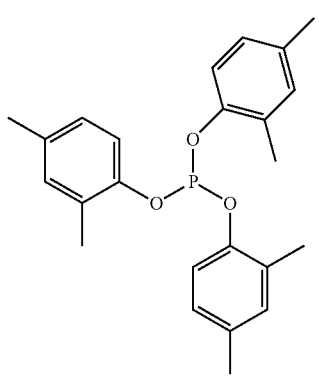

or formula (XIV):

(XIV)

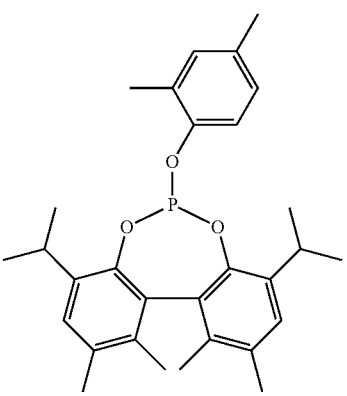

or a mixture thereof;
and the hydrolysis catalyst of formula (I)—is formula (IA2):

(IA2)

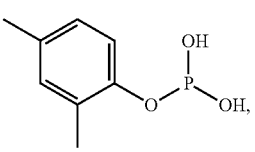

or of formula (IB2):

(IB2)

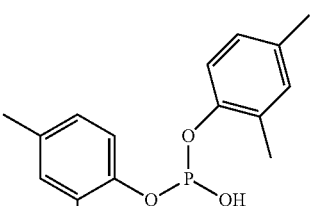

or a mixture thereof.

13. The process of claim 1, wherein the reaction mixture further comprises cyclohexane, toluene, or a combination thereof.

14. The process of claim 1, wherein the reaction mixture further comprises one or more nitriles.

15. The process of claim 14, wherein the nitriles comprise at least one of 3-pentenenitrile and adiponitrile.

* * * * *